US008932834B2

(12) United States Patent
Doi et al.

(10) Patent No.: US 8,932,834 B2
(45) Date of Patent: Jan. 13, 2015

(54) METHOD FOR PRODUCING AN L-AMINO ACID IN A CULTURED BACTERIUM HAVING REDUCED ACTIVITY OF THE ARGININE SUCCINYLTRANSFERASE PATHWAY

(75) Inventors: Hidetaka Doi, Kawasaki (JP); Yoshihiro Usuda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/404,148

(22) Filed: Feb. 24, 2012

(65) Prior Publication Data

US 2012/0219995 A1 Aug. 30, 2012

Related U.S. Application Data

(63) Continuation of application No. PCT/JP2010/061268, filed on Jul. 1, 2010.

(30) Foreign Application Priority Data

Aug. 28, 2009 (JP) .................................. 2009-197575

(51) Int. Cl.
| C12P 13/08 | (2006.01) |
| C12P 13/12 | (2006.01) |
| C12P 13/22 | (2006.01) |
| C12N 1/21 | (2006.01) |
| C12N 9/02 | (2006.01) |
| C12N 9/10 | (2006.01) |
| C12N 9/78 | (2006.01) |
| C12N 9/80 | (2006.01) |

(52) U.S. Cl.
CPC ............... *C12P 13/08* (2013.01); *C12N 9/0008* (2013.01); *C12N 9/1029* (2013.01); *C12N 9/1096* (2013.01); *C12N 9/78* (2013.01); *C12N 9/80* (2013.01); *C12P 13/12* (2013.01); *C12P 13/227* (2013.01); *C12Y 206/01081* (2013.01); *C12Y 305/01096* (2013.01); *C12Y 203/01109* (2013.01); *C12Y 305/03023* (2013.01)
USPC ...................................... 435/115; 435/252.33

(58) Field of Classification Search
None
See application file for complete search history.

(56) References Cited

U.S. PATENT DOCUMENTS

| 6,040,160 | A | * | 3/2000 | Kojima et al. ................. 435/115 |
| 6,911,332 | B2 | | 6/2005 | Usuda et al. |
| 7,026,149 | B2 | | 4/2006 | Usuda et al. |
| 7,029,893 | B2 | | 4/2006 | Usuda et al. |
| 7,060,475 | B2 | | 6/2006 | Usuda et al. |
| 7,192,748 | B2 | | 3/2007 | Usuda et al. |
| 7,220,570 | B2 | | 5/2007 | Usuda et al. |
| 7,229,794 | B2 | | 6/2007 | Park et al. |
| 7,306,933 | B2 | | 12/2007 | Van Dien et al. |
| 7,468,262 | B2 | | 12/2008 | Usuda et al. |
| 7,695,946 | B2 | | 4/2010 | Usuda et al. |
| 7,696,315 | B2 | | 4/2010 | Usuda et al. |
| 7,811,798 | B2 | | 10/2010 | Rybak et al. |
| 7,833,761 | B2 | | 11/2010 | Terashita et al. |
| 8,030,036 | B2 | | 10/2011 | Van Dien et al. |
| 8,076,111 | B2 | | 12/2011 | Fukui et al. |
| 8,080,396 | B2 | | 12/2011 | Shiraga et al. |
| 2005/0233308 | A1 | | 10/2005 | Nishio et al. |
| 2009/0093029 | A1 | | 4/2009 | Usuda et al. |
| 2009/0203090 | A1 | | 8/2009 | Ptitsyn et al. |
| 2009/0246835 | A1 | | 10/2009 | Iwatani et al. |
| 2009/0257647 | A1 | | 10/2009 | Yoshitake et al. |
| 2009/0258399 | A1 | * | 10/2009 | Hashimoto et al. ........... 435/106 |
| 2009/0291478 | A1 | | 11/2009 | Usuda et al. |
| 2010/0047878 | A1 | | 2/2010 | Nagai et al. |
| 2010/0093044 | A1 | | 4/2010 | Terashita et al. |
| 2010/0112647 | A1 | | 5/2010 | Hara et al. |
| 2010/0190217 | A1 | | 7/2010 | Doi et al. |
| 2010/0221792 | A1 | | 9/2010 | Nagai et al. |
| 2011/0014663 | A1 | | 1/2011 | Suzuki et al. |
| 2011/0117613 | A1 | | 5/2011 | Hishino et al. |
| 2011/0201062 | A1 | | 8/2011 | Nishio et al. |

FOREIGN PATENT DOCUMENTS

| EP | 1 715 055 A2 | | 10/2006 |
| EP | 1 715 056 A1 | | 10/2006 |
| WO | WO 2007077041 A1 | * | 7/2007 |
| WO | WO2008/013187 | | 1/2008 |
| WO | WO2008/107277 A1 | | 9/2008 |
| WO | WO2009/011354 A1 | | 1/2009 |
| WO | WO2011/024555 | | 3/2011 |

OTHER PUBLICATIONS

Dauce-Le Reverend et al., Improvement of *Escherichia coli* strains overproducing lysine using recombinant DNA techniques, Eur. J. App. Microbiol. Biotech., 1982,15, 227-31.*

Lu, Pathways and regulation of bacterial arginine metabolism and perspectives for obtaining arginine overproducing strains, Appl. Microbiol. Biotechnol., 2006, 70, 261-72.*

GenBank AAC74817.1 (GI:1788043), 2007, www.ncbi.nlm.nih.gov.*

Cohen, Microbial Biochemistry, Chapter XXII, The Aspartic acid family of amino acids. Biosynthesis, 2004.*

(Continued)

*Primary Examiner* — Rebecca Prouty
*Assistant Examiner* — Todd M Epstein
(74) *Attorney, Agent, or Firm* — Shelly Guest Cermak; Cermak Nakajima & McGowan LLP

(57) ABSTRACT

A method for producing an L-amino acid which includes the steps of culturing a bacterium belonging to the family Enterobacteriaceae and having an L-amino acid producing ability in a medium to produce and accumulate an L-amino acid in the medium, and collecting the L-amino acid from the medium, wherein the bacterium has been modified so that an activity or activities of one or two or more enzymes of the arginine succinyltransferase pathway, such as arginine succinyltransferase, succinylarginine dihydrolase, succinylornithine aminotransferase, succinylglutamate-semialdehyde dehydrogenase, and succinylglutamate desuccinylase, is/are decreased.

5 Claims, No Drawings

(56) References Cited

OTHER PUBLICATIONS

Schneider, B. L., et al., "Arginine Catabolism and the Arginine Succinyltransferase Pathway in *Escherichia coli*," J. Bacteriol. 1998;180(16):4278-4286.

International Search Report for PCT Patent App. No. PCT/JP2010/061268 (Aug. 10, 2010).

Kiupakis, A. K., et al., "ArgR-Independent Induction and ArgR-Dependent Superinduction of the *astCADBE* Operon in *Escherichia coli*," J. Bacteriol. 2002;184(11):2940-2950.

Shirai, H., et al., "Prediction of the structure and function of AstA and AstB, the first two enzymes of the arginine succinyltransferase pathway of arginine catabolism," FEBS Lett. 2003;555:505-510.

* cited by examiner

```
                        SEQUENCE LISTING

<160> NUMBER OF SEQ ID NOS: 12

<210> SEQ ID NO 1
<211> LENGTH: 1035
<212> TYPE: DNA
<213> ORGANISM: Escherichia coli
<220> FEATURE:
<221> NAME/KEY: CDS
<222> LOCATION: (1)..(1032)

<400> SEQUENCE: 1 atg atg gtc atc cgt ccc gtt gag cga tca gat gtc tcg gcg ctg atg        48
Met Met Val Ile Arg Pro Val Glu Arg Ser Asp Val Ser Ala Leu Met
1               5                   10                  15 cag ctt gcc agc aaa acg ggc ggc ggc ctg acg tcg ctt ccc gcc aat        96
Gln Leu Ala Ser Lys Thr Gly Gly Gly Leu Thr Ser Leu Pro Ala Asn
            20                  25                  30 gaa gcc acg ctt tcg gcg cgt atc gaa agg gca atc aaa acc tgg caa       144
Glu Ala Thr Leu Ser Ala Arg Ile Glu Arg Ala Ile Lys Thr Trp Gln
        35                  40                  45 ggc gaa ctg ccc aaa agt gag cag ggc tat gtg ttc gtg ctg gaa gat       192
Gly Glu Leu Pro Lys Ser Glu Gln Gly Tyr Val Phe Val Leu Glu Asp
    50                  55                  60 agc gag aca ggc acc gtg gcg ggg att tgt gcc att gag gtg gcg gtt       240
Ser Glu Thr Gly Thr Val Ala Gly Ile Cys Ala Ile Glu Val Ala Val
65                  70                  75                  80 ggg ctg aac gat ccc tgg tac aac tat cgc gtc ggc acg ttg gtt cac       288
Gly Leu Asn Asp Pro Trp Tyr Asn Tyr Arg Val Gly Thr Leu Val His
                85                  90                  95 gcc tca aaa gag ctg aat gtc tat aac gca ttg ccg acg ctg ttt ctc       336
Ala Ser Lys Glu Leu Asn Val Tyr Asn Ala Leu Pro Thr Leu Phe Leu
            100                 105                 110 agt aac gat cac acc ggc agc agc gag ctg tgc acg ctg ttt ctc gac       384
Ser Asn Asp His Thr Gly Ser Ser Glu Leu Cys Thr Leu Phe Leu Asp
        115                 120                 125 ccg gac tgg cgc aaa gag ggc aac ggc tat ttg ctg tcg aaa tcg cgc       432
Pro Asp Trp Arg Lys Glu Gly Asn Gly Tyr Leu Leu Ser Lys Ser Arg
    130                 135                 140 ttt atg ttt atg gcg gct ttt cgc gac aag ttt aat gac aaa gtg gtt       480
Phe Met Phe Met Ala Ala Phe Arg Asp Lys Phe Asn Asp Lys Val Val
145                 150                 155                 160 gct gaa atg cgc ggg gtg att gac gaa cac ggc tat tca ccg ttc tgg       528
Ala Glu Met Arg Gly Val Ile Asp Glu His Gly Tyr Ser Pro Phe Trp
```

```
                        165                 170                 175
caa agc ctc ggt aaa cgc ttc ttt tcg atg gat ttt agc cgc gcc gat         576
Gln Ser Leu Gly Lys Arg Phe Phe Ser Met Asp Phe Ser Arg Ala Asp
            180                 185                 190 ttt ctc tgc ggc acc ggg caa aag gca ttt att gca gaa ctg atg ccg         624
Phe Leu Cys Gly Thr Gly Gln Lys Ala Phe Ile Ala Glu Leu Met Pro
        195                 200                 205 aaa cat ccg atc tat acc cac ttt tta tcc cag gaa gcc cag gac gtc         672
Lys His Pro Ile Tyr Thr His Phe Leu Ser Gln Glu Ala Gln Asp Val
    210                 215                 220 atc ggt cag gta cat ccg caa acc gcg cct gcc cgc gcg gtg ctg gag         720
Ile Gly Gln Val His Pro Gln Thr Ala Pro Ala Arg Ala Val Leu Glu
225                 230                 235                 240 aaa gaa ggt ttt cgc tac cgt aac tat atc gac atc ttt gac ggt ggg         768
Lys Glu Gly Phe Arg Tyr Arg Asn Tyr Ile Asp Ile Phe Asp Gly Gly
                245                 250                 255 ccg acg ctt gag tgt gac atc gac cgc gtg cgc gcc atc cgt aaa agt         816
Pro Thr Leu Glu Cys Asp Ile Asp Arg Val Arg Ala Ile Arg Lys Ser
            260                 265                 270 cgg ctg gtg gaa gtg gca gaa ggg cag cct gcg cag ggc gat ttc cca         864
Arg Leu Val Glu Val Ala Glu Gly Gln Pro Ala Gln Gly Asp Phe Pro
        275                 280                 285 gcc tgc ctg gtc gcc aat gaa aat tat cac cat ttc cgc gtg gtg ctg         912
Ala Cys Leu Val Ala Asn Glu Asn Tyr His His Phe Arg Val Val Leu
    290                 295                 300 gtg cgt acc gat ccg gca acc gag cgt ttg att tta acc gcc gca caa         960
Val Arg Thr Asp Pro Ala Thr Glu Arg Leu Ile Leu Thr Ala Ala Gln
305                 310                 315                 320 ctg gat gcc ctc aaa tgc cac gcc ggg gat cgc gtt cgt ctg gtg cgc        1008
Leu Asp Ala Leu Lys Cys His Ala Gly Asp Arg Val Arg Leu Val Arg
                325                 330                 335 ctg tgc gca gag gag aaa aca gca tga                                    1035
Leu Cys Ala Glu Glu Lys Thr Ala
            340

<210> SEQ ID NO 2
<211> LENGTH: 344
<212> TYPE: PRT
<213> ORGANISM: Escherichia coli

<400> SEQUENCE: 2

Met Met Val Ile Arg Pro Val Glu Arg Ser Asp Val Ser Ala Leu Met
1               5                   10                  15

Gln Leu Ala Ser Lys Thr Gly Gly Leu Thr Ser Leu Pro Ala Asn
            20                  25                  30

Glu Ala Thr Leu Ser Ala Arg Ile Glu Arg Ala Ile Lys Thr Trp Gln
        35                  40                  45

Gly Glu Leu Pro Lys Ser Glu Gln Gly Tyr Val Phe Val Leu Glu Asp
    50                  55                  60

Ser Glu Thr Gly Thr Val Ala Gly Ile Cys Ala Ile Glu Val Ala Val
65                  70                  75                  80

Gly Leu Asn Asp Pro Trp Tyr Asn Tyr Arg Val Gly Thr Leu Val His
                85                  90                  95

Ala Ser Lys Glu Leu Asn Val Tyr Asn Ala Leu Pro Thr Leu Phe Leu
            100                 105                 110

Ser Asn Asp His Thr Gly Ser Ser Glu Leu Cys Thr Leu Phe Leu Asp
        115                 120                 125

Pro Asp Trp Arg Lys Glu Gly Asn Gly Tyr Leu Leu Ser Lys Ser Arg
```

```
                  130                 135                 140
Phe Met Phe Met Ala Ala Phe Arg Asp Lys Phe Asn Asp Lys Val Val
145                 150                 155                 160

Ala Glu Met Arg Gly Val Ile Asp Glu His Gly Tyr Ser Pro Phe Trp
                165                 170                 175

Gln Ser Leu Gly Lys Arg Phe Phe Ser Met Asp Phe Ser Arg Ala Asp
            180                 185                 190

Phe Leu Cys Gly Thr Gly Gln Lys Ala Phe Ile Ala Glu Leu Met Pro
        195                 200                 205

Lys His Pro Ile Tyr Thr His Phe Leu Ser Gln Glu Ala Gln Asp Val
    210                 215                 220

Ile Gly Gln Val His Pro Gln Thr Ala Pro Ala Arg Ala Val Leu Glu
225                 230                 235                 240

Lys Glu Gly Phe Arg Tyr Arg Asn Tyr Ile Asp Ile Phe Asp Gly Gly
                245                 250                 255

Pro Thr Leu Glu Cys Asp Ile Asp Arg Val Arg Ala Ile Arg Lys Ser
            260                 265                 270

Arg Leu Val Glu Val Ala Glu Gly Gln Pro Ala Gln Gly Asp Phe Pro
        275                 280                 285

Ala Cys Leu Val Ala Asn Glu Asn Tyr His His Phe Arg Val Val Leu
    290                 295                 300

Val Arg Thr Asp Pro Ala Thr Glu Arg Leu Ile Leu Thr Ala Ala Gln
305                 310                 315                 320

Leu Asp Ala Leu Lys Cys His Ala Gly Asp Arg Val Arg Leu Val Arg
                325                 330                 335

Leu Cys Ala Glu Glu Lys Thr Ala
            340

<210> SEQ ID NO 3
<211> LENGTH: 1344
<212> TYPE: DNA
<213> ORGANISM: Escherichia coli
<220> FEATURE:
<221> NAME/KEY: CDS
<222> LOCATION: (1)..(1341)

<400> SEQUENCE: 3 atg aac gcc tgg gaa gtc aat ttc gac ggg ctg gta ggg ctg acg cat      48
Met Asn Ala Trp Glu Val Asn Phe Asp Gly Leu Val Gly Leu Thr His
1               5                   10                  15 cat tac gcg ggc ctg tcg ttt ggt aat gaa gcc tct acc cgt cac cgt      96
His Tyr Ala Gly Leu Ser Phe Gly Asn Glu Ala Ser Thr Arg His Arg
            20                  25                  30 ttt cag gtg tct aac ccg cga ctg gcg gcg aag cag ggc tta ctg aaa     144
Phe Gln Val Ser Asn Pro Arg Leu Ala Ala Lys Gln Gly Leu Leu Lys
        35                  40                  45 atg aaa gcc ctt gcc gat gcg gga ttc ccc cag gcc gtg atc ccg ccg     192
Met Lys Ala Leu Ala Asp Ala Gly Phe Pro Gln Ala Val Ile Pro Pro
    50                  55                  60 cac gag cgt ccg ttt att ccg gtg ctg cgt cag ttg gga ttc agt ggt     240
His Glu Arg Pro Phe Ile Pro Val Leu Arg Gln Leu Gly Phe Ser Gly
65                  70                  75                  80 agc gat gag cag gta ctg gaa aaa gtt gca cgc cag gca ccg cac tgg     288
Ser Asp Glu Gln Val Leu Glu Lys Val Ala Arg Gln Ala Pro His Trp
                85                  90                  95 ctt tcc agc gtc agt tcc gct tcg cca atg tgg gta gcc aat gcg gca     336
Leu Ser Ser Val Ser Ser Ala Ser Pro Met Trp Val Ala Asn Ala Ala
            100                 105                 110
```

```
acg atc gcg cca tct gcc gat acg ctg gat ggc aaa gtg cat ctc acc      384
Thr Ile Ala Pro Ser Ala Asp Thr Leu Asp Gly Lys Val His Leu Thr
        115                 120                 125 gtt gcc aac ctg aac aat aaa ttt cac cgt tcg ctg gaa gcg ccc gtc      432
Val Ala Asn Leu Asn Asn Lys Phe His Arg Ser Leu Glu Ala Pro Val
        130                 135                 140 act gaa tcg ctg tta aaa gcg att ttt aac gac gaa gag aaa ttt agc      480
Thr Glu Ser Leu Leu Lys Ala Ile Phe Asn Asp Glu Glu Lys Phe Ser
145                 150                 155                 160 gtc cat tcg gcg ttg cca cag gta gcg ttg ctc ggt gat gag ggg gcg      528
Val His Ser Ala Leu Pro Gln Val Ala Leu Leu Gly Asp Glu Gly Ala
                165                 170                 175 gca aac cac aat cgt ctc ggc ggt cat tac ggt gaa ccg ggt atg caa      576
Ala Asn His Asn Arg Leu Gly Gly His Tyr Gly Glu Pro Gly Met Gln
        180                 185                 190 ctt ttt gtc tac ggg cga gaa gaa ggc aat gat acc cgg cct tcc cgt      624
Leu Phe Val Tyr Gly Arg Glu Glu Gly Asn Asp Thr Arg Pro Ser Arg
        195                 200                 205 tat ccg gcg cga cag act cgc gaa gcc agc gag gcg gtg gca agg ctg      672
Tyr Pro Ala Arg Gln Thr Arg Glu Ala Ser Glu Ala Val Ala Arg Leu
        210                 215                 220 aat cag gtg aat ccc caa cag gtg att ttc gcc cag caa aac ccg gac      720
Asn Gln Val Asn Pro Gln Gln Val Ile Phe Ala Gln Gln Asn Pro Asp
225                 230                 235                 240 gtt atc gac cag ggc gtt ttt cat aat gac gtg att gcc gtg agt aac      768
Val Ile Asp Gln Gly Val Phe His Asn Asp Val Ile Ala Val Ser Asn
                245                 250                 255 cgc cag gtg ctg ttt tgc cac caa cag gcg ttc gct cgc cag tca cag      816
Arg Gln Val Leu Phe Cys His Gln Gln Ala Phe Ala Arg Gln Ser Gln
        260                 265                 270 tta ctg gca aac ctg cgt gcg cgg gtc aat ggt ttt atg gcg ata gaa      864
Leu Leu Ala Asn Leu Arg Ala Arg Val Asn Gly Phe Met Ala Ile Glu
        275                 280                 285 gtt ccg gca act cag gtt tcc gtg tct gat acg gtg tct acc tat ctg      912
Val Pro Ala Thr Gln Val Ser Val Ser Asp Thr Val Ser Thr Tyr Leu
        290                 295                 300 ttt aac agc caa ctg ctg agc cgc gat gat ggt tcc atg atg ttg gtg      960
Phe Asn Ser Gln Leu Leu Ser Arg Asp Asp Gly Ser Met Met Leu Val
305                 310                 315                 320 ctg cct cag gag tgt cgg gaa cac gcc gga gta tgg ggt tat ctc aat     1008
Leu Pro Gln Glu Cys Arg Glu His Ala Gly Val Trp Gly Tyr Leu Asn
                325                 330                 335 gaa ctc ctt gcc gct gac aac ccg att agc gaa cta aaa gtc ttt gat     1056
Glu Leu Leu Ala Ala Asp Asn Pro Ile Ser Glu Leu Lys Val Phe Asp
        340                 345                 350 tta cgt gaa agc atg gcg aat ggc ggc ggc ccg gcg tgc ctg cgg ttg     1104
Leu Arg Glu Ser Met Ala Asn Gly Gly Gly Pro Ala Cys Leu Arg Leu
        355                 360                 365 cgg gtg gta ttg aca gaa gaa gaa cgc cgg gcg gtg aat ccg gcg gtg     1152
Arg Val Val Leu Thr Glu Glu Glu Arg Arg Ala Val Asn Pro Ala Val
        370                 375                 380 atg atg aac gat acg ctg ttt aat gcg ctc aat gac tgg gtg gat cgt     1200
Met Met Asn Asp Thr Leu Phe Asn Ala Leu Asn Asp Trp Val Asp Arg
385                 390                 395                 400 tac tac cgc gat cgc ctt act gct gcc gat ctg gcc gac ccg caa ttg     1248
Tyr Tyr Arg Asp Arg Leu Thr Ala Ala Asp Leu Ala Asp Pro Gln Leu
                405                 410                 415 ctg cgc gaa ggg cgg gaa gca ctg gat gta ttg agc caa tta ctg aat     1296
Leu Arg Glu Gly Arg Glu Ala Leu Asp Val Leu Ser Gln Leu Leu Asn
```

```
                       420             425             430
ctc ggt tcg gtt tat ccg ttc cag cgc gag gga ggg ggc aat gga taa   1344
Leu Gly Ser Val Tyr Pro Phe Gln Arg Glu Gly Gly Gly Asn Gly
        435             440             445
```

<210> SEQ ID NO 4
<211> LENGTH: 447
<212> TYPE: PRT
<213> ORGANISM: Escherichia coli

<400> SEQUENCE: 4

```
Met Asn Ala Trp Glu Val Asn Phe Asp Gly Leu Val Gly Leu Thr His
1               5                   10                  15

His Tyr Ala Gly Leu Ser Phe Gly Asn Glu Ala Ser Thr Arg His Arg
            20                  25                  30

Phe Gln Val Ser Asn Pro Arg Leu Ala Ala Lys Gln Gly Leu Leu Lys
        35                  40                  45

Met Lys Ala Leu Ala Asp Ala Gly Phe Pro Gln Ala Val Ile Pro Pro
    50                  55                  60

His Glu Arg Pro Phe Ile Pro Val Leu Arg Gln Leu Gly Phe Ser Gly
65                  70                  75                  80

Ser Asp Glu Gln Val Leu Glu Lys Val Ala Arg Gln Ala Pro His Trp
                85                  90                  95

Leu Ser Ser Val Ser Ser Ala Ser Pro Met Trp Val Ala Asn Ala Ala
            100                 105                 110

Thr Ile Ala Pro Ser Ala Asp Thr Leu Asp Gly Lys Val His Leu Thr
        115                 120                 125

Val Ala Asn Leu Asn Asn Lys Phe His Arg Ser Leu Glu Ala Pro Val
    130                 135                 140

Thr Glu Ser Leu Leu Lys Ala Ile Phe Asn Asp Glu Glu Lys Phe Ser
145                 150                 155                 160

Val His Ser Ala Leu Pro Gln Val Ala Leu Leu Gly Asp Glu Gly Ala
                165                 170                 175

Ala Asn His Asn Arg Leu Gly Gly His Tyr Gly Glu Pro Gly Met Gln
            180                 185                 190

Leu Phe Val Tyr Gly Arg Glu Glu Gly Asn Asp Thr Arg Pro Ser Arg
        195                 200                 205

Tyr Pro Ala Arg Gln Thr Arg Glu Ala Ser Glu Ala Val Ala Arg Leu
    210                 215                 220

Asn Gln Val Asn Pro Gln Gln Val Ile Phe Ala Gln Gln Asn Pro Asp
225                 230                 235                 240

Val Ile Asp Gln Gly Val Phe His Asn Asp Val Ile Ala Val Ser Asn
                245                 250                 255

Arg Gln Val Leu Phe Cys His Gln Gln Ala Phe Ala Arg Gln Ser Gln
            260                 265                 270

Leu Leu Ala Asn Leu Arg Ala Arg Val Asn Gly Phe Met Ala Ile Glu
        275                 280                 285

Val Pro Ala Thr Gln Val Ser Val Ser Asp Thr Val Ser Thr Tyr Leu
    290                 295                 300

Phe Asn Ser Gln Leu Leu Ser Arg Asp Asp Gly Ser Met Met Leu Val
305                 310                 315                 320

Leu Pro Gln Glu Cys Arg Glu His Ala Gly Val Trp Gly Tyr Leu Asn
                325                 330                 335

Glu Leu Leu Ala Ala Asp Asn Pro Ile Ser Glu Leu Lys Val Phe Asp
            340                 345                 350
```

```
Leu Arg Glu Ser Met Ala Asn Gly Gly Pro Ala Cys Leu Arg Leu
        355                 360                 365

Arg Val Val Leu Thr Glu Glu Arg Arg Ala Val Asn Pro Ala Val
    370                 375                 380

Met Met Asn Asp Thr Leu Phe Asn Ala Leu Asn Asp Trp Val Asp Arg
385                 390                 395                 400

Tyr Tyr Arg Asp Arg Leu Thr Ala Ala Asp Leu Ala Asp Pro Gln Leu
                405                 410                 415

Leu Arg Glu Gly Arg Glu Ala Leu Asp Val Leu Ser Gln Leu Leu Asn
                420                 425                 430

Leu Gly Ser Val Tyr Pro Phe Gln Arg Glu Gly Gly Gly Asn Gly
        435                 440                 445
```

```
<210> SEQ ID NO 5
<211> LENGTH: 1221
<212> TYPE: DNA
<213> ORGANISM: Escherichia coli
<220> FEATURE:
<221> NAME/KEY: CDS
<222> LOCATION: (1)..(1218)

<400> SEQUENCE: 5
```

| | | | | | | | | | | | | | | | | |
|---|---|---|---|---|---|---|---|---|---|---|---|---|---|---|---|---|
| atg | tct | cag | cca | att | acg | cgt | gaa | aac | ttt | gat | gaa | tgg | atg | ata | cct | 48 |
| Met | Ser | Gln | Pro | Ile | Thr | Arg | Glu | Asn | Phe | Asp | Glu | Trp | Met | Ile | Pro | |
| 1 | | | | 5 | | | | | 10 | | | | | 15 | | |
| gtt | tac | gct | ccg | gca | ccc | ttt | ata | ccg | gta | cgt | ggc | gaa | ggt | tcg | cgc | 96 |
| Val | Tyr | Ala | Pro | Ala | Pro | Phe | Ile | Pro | Val | Arg | Gly | Glu | Gly | Ser | Arg | |
| | | | 20 | | | | | 25 | | | | | 30 | | | |
| ttg | tgg | gat | cag | cag | ggg | aaa | gag | tat | atc | gac | ttc | gcg | ggt | ggc | att | 144 |
| Leu | Trp | Asp | Gln | Gln | Gly | Lys | Glu | Tyr | Ile | Asp | Phe | Ala | Gly | Gly | Ile | |
| | | 35 | | | | | 40 | | | | | 45 | | | | |
| gcg | gtg | aac | gcg | ctg | ggc | cat | gcg | cat | ccg | gaa | ctg | cgt | gaa | gcg | ctg | 192 |
| Ala | Val | Asn | Ala | Leu | Gly | His | Ala | His | Pro | Glu | Leu | Arg | Glu | Ala | Leu | |
| | 50 | | | | | 55 | | | | | 60 | | | | | |
| aac | gaa | cag | gcg | agt | aag | ttc | tgg | cat | acc | ggc | aac | ggt | tac | acc | aac | 240 |
| Asn | Glu | Gln | Ala | Ser | Lys | Phe | Trp | His | Thr | Gly | Asn | Gly | Tyr | Thr | Asn | |
| 65 | | | | | 70 | | | | | 75 | | | | | 80 | |
| gag | ccg | gta | ctg | cga | ctg | gcg | aaa | aaa | ttg | atc | gac | gcc | acg | ttt | gcc | 288 |
| Glu | Pro | Val | Leu | Arg | Leu | Ala | Lys | Lys | Leu | Ile | Asp | Ala | Thr | Phe | Ala | |
| | | | | 85 | | | | | 90 | | | | | 95 | | |
| gat | cgc | gtc | ttc | ttt | tgt | aac | tcc | ggt | gcg | gaa | gcc | aac | gaa | gcg | gcg | 336 |
| Asp | Arg | Val | Phe | Phe | Cys | Asn | Ser | Gly | Ala | Glu | Ala | Asn | Glu | Ala | Ala | |
| | | | 100 | | | | | 105 | | | | | 110 | | | |
| cta | aaa | ctg | gcg | cgt | aaa | ttc | gct | cac | gac | cgc | tac | ggc | agc | cat | aag | 384 |
| Leu | Lys | Leu | Ala | Arg | Lys | Phe | Ala | His | Asp | Arg | Tyr | Gly | Ser | His | Lys | |
| | | 115 | | | | | 120 | | | | | 125 | | | | |
| agc | ggc | atc | gtg | gcg | ttc | aaa | aat | gcg | ttt | cat | ggt | cgc | acg | ctg | ttt | 432 |
| Ser | Gly | Ile | Val | Ala | Phe | Lys | Asn | Ala | Phe | His | Gly | Arg | Thr | Leu | Phe | |
| | 130 | | | | | 135 | | | | | 140 | | | | | |
| act | gtc | agt | gcg | ggt | ggg | cag | cca | gcc | tat | tca | cag | gat | ttt | gcg | cca | 480 |
| Thr | Val | Ser | Ala | Gly | Gly | Gln | Pro | Ala | Tyr | Ser | Gln | Asp | Phe | Ala | Pro | |
| 145 | | | | | 150 | | | | | 155 | | | | | 160 | |
| ctg | ccg | gcg | gat | att | cgt | cat | gct | gca | tat | aac | gat | att | aac | tct | gcc | 528 |
| Leu | Pro | Ala | Asp | Ile | Arg | His | Ala | Ala | Tyr | Asn | Asp | Ile | Asn | Ser | Ala | |
| | | | | 165 | | | | | 170 | | | | | 175 | | |
| agc | gcg | ctg | att | gac | gac | tct | acc | tgt | gcg | gtg | att | gtc | gaa | ccc | atc | 576 |
| Ser | Ala | Leu | Ile | Asp | Asp | Ser | Thr | Cys | Ala | Val | Ile | Val | Glu | Pro | Ile | |
| | | | 180 | | | | | 185 | | | | | 190 | | | |
| cag | ggg | gaa | ggc | ggt | gtg | gtg | cca | gcc | agc | aac | gcg | ttt | tta | caa | ggt | 624 |

```
Gln Gly Glu Gly Gly Val Val Pro Ala Ser Asn Ala Phe Leu Gln Gly
            195                 200                 205 ctg cgt gaa ttg tgt aac cgc cac aat gcg ctg ttg att ttt gat gaa      672
Leu Arg Glu Leu Cys Asn Arg His Asn Ala Leu Leu Ile Phe Asp Glu
210                 215                 220 gta caa acc ggc gtc ggg cgc acc ggg gaa ctg tat gcc tat atg cac      720
Val Gln Thr Gly Val Gly Arg Thr Gly Glu Leu Tyr Ala Tyr Met His
225                 230                 235                 240 tac ggc gtg acg cct gat ctg tta act acc gcc aaa gcg ctg ggc ggc      768
Tyr Gly Val Thr Pro Asp Leu Leu Thr Thr Ala Lys Ala Leu Gly Gly
                245                 250                 255 ggt ttc ccg gtc ggt gcg ttg ttg gca acc gaa gag tgc gcc cgc gtg      816
Gly Phe Pro Val Gly Ala Leu Leu Ala Thr Glu Glu Cys Ala Arg Val
            260                 265                 270 atg acc gtt ggc act cat ggc acc acc tat ggc ggt aat ccg ctg gcc      864
Met Thr Val Gly Thr His Gly Thr Thr Tyr Gly Gly Asn Pro Leu Ala
275                 280                 285 tcg gcg gtg gca ggc aaa gtg ctg gag ctc atc aac aca cca gag atg      912
Ser Ala Val Ala Gly Lys Val Leu Glu Leu Ile Asn Thr Pro Glu Met
290                 295                 300 ctt aat ggc gtt aaa cag cgt cac gac tgg ttt gtt gag cgt ctt aat      960
Leu Asn Gly Val Lys Gln Arg His Asp Trp Phe Val Glu Arg Leu Asn
305                 310                 315                 320 act att aat cac cgc tat ggt ttg ttc agt gaa gtt cgc ggc tta ggt     1008
Thr Ile Asn His Arg Tyr Gly Leu Phe Ser Glu Val Arg Gly Leu Gly
                325                 330                 335 ttg ctg att ggc tgt gta ctg aat gcc gat tac gcc ggg caa gcg aaa     1056
Leu Leu Ile Gly Cys Val Leu Asn Ala Asp Tyr Ala Gly Gln Ala Lys
            340                 345                 350 cag atc tct cag gaa gcg gcg aaa gca ggc gtg atg gta ctg att gcg     1104
Gln Ile Ser Gln Glu Ala Ala Lys Ala Gly Val Met Val Leu Ile Ala
355                 360                 365 ggt ggc aac gtg gtg cgt ttt gcg cct gcg ctc aat gtc agc gaa gaa     1152
Gly Gly Asn Val Val Arg Phe Ala Pro Ala Leu Asn Val Ser Glu Glu
370                 375                 380 gag gtg acg acc gga ctg gat cgc ttt gca gct gct tgc gaa cac ttt     1200
Glu Val Thr Thr Gly Leu Asp Arg Phe Ala Ala Ala Cys Glu His Phe
385                 390                 395                 400 gtt agc cga ggt tca tca tga                                         1221
Val Ser Arg Gly Ser Ser
                405
```

<210> SEQ ID NO 6
<211> LENGTH: 406
<212> TYPE: PRT
<213> ORGANISM: Escherichia coli

<400> SEQUENCE: 6

```
Met Ser Gln Pro Ile Thr Arg Glu Asn Phe Asp Glu Trp Met Ile Pro
1               5                   10                  15

Val Tyr Ala Pro Ala Pro Phe Ile Pro Val Arg Gly Glu Gly Ser Arg
            20                  25                  30

Leu Trp Asp Gln Gln Gly Lys Glu Tyr Ile Asp Phe Ala Gly Gly Ile
        35                  40                  45

Ala Val Asn Ala Leu Gly His Ala His Pro Glu Leu Arg Glu Ala Leu
    50                  55                  60

Asn Glu Gln Ala Ser Lys Phe Trp His Thr Gly Asn Gly Tyr Thr Asn
65                  70                  75                  80

Glu Pro Val Leu Arg Leu Ala Lys Lys Leu Ile Asp Ala Thr Phe Ala
```

```
                85                  90                  95

Asp Arg Val Phe Phe Cys Asn Ser Gly Ala Glu Ala Asn Glu Ala Ala
            100                 105                 110

Leu Lys Leu Ala Arg Lys Phe Ala His Asp Arg Tyr Gly Ser His Lys
        115                 120                 125

Ser Gly Ile Val Ala Phe Lys Asn Ala Phe His Gly Arg Thr Leu Phe
    130                 135                 140

Thr Val Ser Ala Gly Gly Gln Pro Ala Tyr Ser Gln Asp Phe Ala Pro
145                 150                 155                 160

Leu Pro Ala Asp Ile Arg His Ala Ala Tyr Asn Asp Ile Asn Ser Ala
                165                 170                 175

Ser Ala Leu Ile Asp Asp Ser Thr Cys Ala Val Ile Val Glu Pro Ile
            180                 185                 190

Gln Gly Glu Gly Gly Val Val Pro Ala Ser Asn Ala Phe Leu Gln Gly
        195                 200                 205

Leu Arg Glu Leu Cys Asn Arg His Asn Ala Leu Leu Ile Phe Asp Glu
    210                 215                 220

Val Gln Thr Gly Val Gly Arg Thr Gly Glu Leu Tyr Ala Tyr Met His
225                 230                 235                 240

Tyr Gly Val Thr Pro Asp Leu Leu Thr Thr Ala Lys Ala Leu Gly Gly
                245                 250                 255

Gly Phe Pro Val Gly Ala Leu Leu Ala Thr Glu Glu Cys Ala Arg Val
            260                 265                 270

Met Thr Val Gly Thr His Gly Thr Thr Tyr Gly Gly Asn Pro Leu Ala
        275                 280                 285

Ser Ala Val Ala Gly Lys Val Leu Glu Leu Ile Asn Thr Pro Glu Met
    290                 295                 300

Leu Asn Gly Val Lys Gln Arg His Asp Trp Phe Val Glu Arg Leu Asn
305                 310                 315                 320

Thr Ile Asn His Arg Tyr Gly Leu Phe Ser Glu Val Arg Gly Leu Gly
                325                 330                 335

Leu Leu Ile Gly Cys Val Leu Asn Ala Asp Tyr Ala Gly Gln Ala Lys
            340                 345                 350

Gln Ile Ser Gln Glu Ala Ala Lys Ala Gly Val Met Val Leu Ile Ala
        355                 360                 365

Gly Gly Asn Val Val Arg Phe Ala Pro Ala Leu Asn Val Ser Glu Glu
    370                 375                 380

Glu Val Thr Thr Gly Leu Asp Arg Phe Ala Ala Ala Cys Glu His Phe
385                 390                 395                 400

Val Ser Arg Gly Ser Ser
                405

<210> SEQ ID NO 7
<211> LENGTH: 1479
<212> TYPE: DNA
<213> ORGANISM: Escherichia coli
<220> FEATURE:
<221> NAME/KEY: CDS
<222> LOCATION: (1)..(1476)

<400> SEQUENCE: 7 atg act tta tgg att aac ggt gac tgg ata acg ggc cag ggc gca tcg     48
Met Thr Leu Trp Ile Asn Gly Asp Trp Ile Thr Gly Gln Gly Ala Ser
1               5                   10                  15 cgt gtg aag cgt aat ccg gta tcg ggc gag gtg tta tgg caa ggc aat     96
Arg Val Lys Arg Asn Pro Val Ser Gly Glu Val Leu Trp Gln Gly Asn
```

```
               20                  25                  30
gat gcc gat gcc gct cag gtc gag cag gct tgt cgg gca gcc cgt gcg     144
Asp Ala Asp Ala Ala Gln Val Glu Gln Ala Cys Arg Ala Ala Arg Ala
         35                  40                  45 gcg ttt ccg cgc tgg gcg cgg ctt tca ttt gct gaa cgt cat gcc gtt     192
Ala Phe Pro Arg Trp Ala Arg Leu Ser Phe Ala Glu Arg His Ala Val
 50                  55                  60 gtc gaa cgc ttt gcc gca ctg ctg gaa agc aat aaa gcc gaa tta acc     240
Val Glu Arg Phe Ala Ala Leu Leu Glu Ser Asn Lys Ala Glu Leu Thr
 65                  70                  75                  80 gcg att att gcc aga gaa acg ggt aag ccg cgc tgg gaa gcg gca acc     288
Ala Ile Ile Ala Arg Glu Thr Gly Lys Pro Arg Trp Glu Ala Ala Thr
             85                  90                  95 gaa gtg acg gcg atg atc aat aaa atc gcg ata tca att aag gcg tat     336
Glu Val Thr Ala Met Ile Asn Lys Ile Ala Ile Ser Ile Lys Ala Tyr
            100                 105                 110 cac gtt cgt acc ggc gag cag cgt agt gaa atg ccg gac ggc gcg gcg     384
His Val Arg Thr Gly Glu Gln Arg Ser Glu Met Pro Asp Gly Ala Ala
            115                 120                 125 agc ctg cga cat cgc ccg cac ggc gtg ctg gcg gtg ttt ggg ccg tat     432
Ser Leu Arg His Arg Pro His Gly Val Leu Ala Val Phe Gly Pro Tyr
        130                 135                 140 aat ttc cct ggt cat ttg ccg aac gga cat atc gtt ccg gca ttg ctg     480
Asn Phe Pro Gly His Leu Pro Asn Gly His Ile Val Pro Ala Leu Leu
145                 150                 155                 160 gca ggt aac acc att atc ttt aaa ccc agc gaa ctg aca ccg tgg agt     528
Ala Gly Asn Thr Ile Ile Phe Lys Pro Ser Glu Leu Thr Pro Trp Ser
                165                 170                 175 ggc gaa gcg gta atg cgt tta tgg cag cag gct ggc ttg ccg cca ggc     576
Gly Glu Ala Val Met Arg Leu Trp Gln Gln Ala Gly Leu Pro Pro Gly
            180                 185                 190 gtg ctg aac ctg gtg cag ggc ggg cgt gaa acg ggt cag gcg ctg agt     624
Val Leu Asn Leu Val Gln Gly Gly Arg Glu Thr Gly Gln Ala Leu Ser
        195                 200                 205 gcg ctg gag gat ctc gac ggt ttg ctg ttt acc ggt agc gcc aat aca     672
Ala Leu Glu Asp Leu Asp Gly Leu Leu Phe Thr Gly Ser Ala Asn Thr
    210                 215                 220 ggc tac cag ttg cat cgc cag ctc tcc ggt cag ccg gag aaa att ctc     720
Gly Tyr Gln Leu His Arg Gln Leu Ser Gly Gln Pro Glu Lys Ile Leu
225                 230                 235                 240 gcc ctt gag atg ggc ggt aat aat ccg cta att atc gat gag gtg gcg     768
Ala Leu Glu Met Gly Gly Asn Asn Pro Leu Ile Ile Asp Glu Val Ala
                245                 250                 255 gat atc gac gcg gct gtc cat ctg acc att cag tcg gcg ttt gtc aca     816
Asp Ile Asp Ala Ala Val His Leu Thr Ile Gln Ser Ala Phe Val Thr
            260                 265                 270 gcc ggt caa cgc tgc acc tgc gcc cgc cgt tta ttg ctg aaa agc ggg     864
Ala Gly Gln Arg Cys Thr Cys Ala Arg Arg Leu Leu Leu Lys Ser Gly
        275                 280                 285 gcg cag ggc gat gcg ttt ctt gct cgt ctg gtt gcc gtc agc cag cga     912
Ala Gln Gly Asp Ala Phe Leu Ala Arg Leu Val Ala Val Ser Gln Arg
    290                 295                 300 tta acg ccg ggc aac tgg gat gac gaa ccg cag ccg ttt att ggc ggg     960
Leu Thr Pro Gly Asn Trp Asp Asp Glu Pro Gln Pro Phe Ile Gly Gly
305                 310                 315                 320 ctg att tct gaa cag gcc gca cag cag gtg gtt act gca tgg cag caa    1008
Leu Ile Ser Glu Gln Ala Ala Gln Gln Val Val Thr Ala Trp Gln Gln
                325                 330                 335 ctg gaa gcg atg ggc gga cga ccc ctg ctt gcg ccg cgc tta tta caa    1056
```

```
              Leu Glu Ala Met Gly Gly Arg Pro Leu Leu Ala Pro Arg Leu Leu Gln
                              340                 345                 350 gca ggg aca tcg ttg ctg acg ccg ggg atc att gaa atg aca ggc gtt      1104
Ala Gly Thr Ser Leu Leu Thr Pro Gly Ile Ile Glu Met Thr Gly Val
            355                 360                 365 gct ggc gta cca gat gaa gag gtg ttc gga ccg tta ttg cgc gtc tgg      1152
Ala Gly Val Pro Asp Glu Glu Val Phe Gly Pro Leu Leu Arg Val Trp
370                 375                 380 cgt tat gat act ttc gat gaa gcg att cga atg gcg aat aac act cgc      1200
Arg Tyr Asp Thr Phe Asp Glu Ala Ile Arg Met Ala Asn Asn Thr Arg
385                 390                 395                 400 ttc gga ctc tct tgc ggt ctg gtt tcc ccc gag cgg gaa aag ttc gat      1248
Phe Gly Leu Ser Cys Gly Leu Val Ser Pro Glu Arg Glu Lys Phe Asp
                405                 410                 415 caa ctg ttg ctg gag gcg cgg gcg ggg att gtt aac tgg aac aaa ccg      1296
Gln Leu Leu Leu Glu Ala Arg Ala Gly Ile Val Asn Trp Asn Lys Pro
            420                 425                 430 ctt acc ggt gct gcc agt acc gcg cca ttc ggc ggc att ggt gct tcc      1344
Leu Thr Gly Ala Ala Ser Thr Ala Pro Phe Gly Gly Ile Gly Ala Ser
        435                 440                 445 ggt aac cat cgc ccc agc gcc tgg tat gcc gca gat tac tgc gca tgg      1392
Gly Asn His Arg Pro Ser Ala Trp Tyr Ala Ala Asp Tyr Cys Ala Trp
450                 455                 460 ccg atg gcg agc ctg gag tcg gac tcg tta aca ttg ccc gcc acg ctt      1440
Pro Met Ala Ser Leu Glu Ser Asp Ser Leu Thr Leu Pro Ala Thr Leu
465                 470                 475                 480 aac ccc ggg ctg gat ttt tcc gat gag gtg gtg cga tga                  1479
Asn Pro Gly Leu Asp Phe Ser Asp Glu Val Val Arg
                485                 490

<210> SEQ ID NO 8
<211> LENGTH: 492
<212> TYPE: PRT
<213> ORGANISM: Escherichia coli

<400> SEQUENCE: 8

Met Thr Leu Trp Ile Asn Gly Asp Trp Ile Thr Gly Gln Gly Ala Ser
1               5                   10                  15

Arg Val Lys Arg Asn Pro Val Ser Gly Glu Val Leu Trp Gln Gly Asn
                20                  25                  30

Asp Ala Asp Ala Ala Gln Val Glu Gln Ala Cys Arg Ala Ala Arg Ala
            35                  40                  45

Ala Phe Pro Arg Trp Ala Arg Leu Ser Phe Ala Glu Arg His Ala Val
        50                  55                  60

Val Glu Arg Phe Ala Ala Leu Leu Glu Ser Asn Lys Ala Glu Leu Thr
65                  70                  75                  80

Ala Ile Ile Ala Arg Glu Thr Gly Lys Pro Arg Trp Glu Ala Ala Thr
                85                  90                  95

Glu Val Thr Ala Met Ile Asn Lys Ile Ala Ile Ser Ile Lys Ala Tyr
            100                 105                 110

His Val Arg Thr Gly Glu Gln Arg Ser Glu Met Pro Asp Gly Ala Ala
        115                 120                 125

Ser Leu Arg His Arg Pro His Gly Val Leu Ala Val Phe Gly Pro Tyr
    130                 135                 140

Asn Phe Pro Gly His Leu Pro Asn Gly His Ile Val Pro Ala Leu Leu
145                 150                 155                 160

Ala Gly Asn Thr Ile Ile Phe Lys Pro Ser Glu Leu Thr Pro Trp Ser
                165                 170                 175
```

```
Gly Glu Ala Val Met Arg Leu Trp Gln Gln Ala Gly Leu Pro Pro Gly
                180                 185                 190

Val Leu Asn Leu Val Gln Gly Arg Glu Thr Gly Gln Ala Leu Ser
            195                 200                 205

Ala Leu Glu Asp Leu Asp Gly Leu Leu Phe Thr Gly Ser Ala Asn Thr
    210                 215                 220

Gly Tyr Gln Leu His Arg Gln Leu Ser Gly Gln Pro Glu Lys Ile Leu
225                 230                 235                 240

Ala Leu Glu Met Gly Gly Asn Asn Pro Leu Ile Ile Asp Glu Val Ala
                245                 250                 255

Asp Ile Asp Ala Ala Val His Leu Thr Ile Gln Ser Ala Phe Val Thr
            260                 265                 270

Ala Gly Gln Arg Cys Thr Cys Ala Arg Arg Leu Leu Leu Lys Ser Gly
        275                 280                 285

Ala Gln Gly Asp Ala Phe Leu Ala Arg Leu Val Ala Val Ser Gln Arg
    290                 295                 300

Leu Thr Pro Gly Asn Trp Asp Asp Glu Pro Gln Pro Phe Ile Gly Gly
305                 310                 315                 320

Leu Ile Ser Glu Gln Ala Ala Gln Gln Val Val Thr Ala Trp Gln Gln
                325                 330                 335

Leu Glu Ala Met Gly Gly Arg Pro Leu Leu Ala Pro Arg Leu Leu Gln
            340                 345                 350

Ala Gly Thr Ser Leu Leu Thr Pro Gly Ile Ile Glu Met Thr Gly Val
        355                 360                 365

Ala Gly Val Pro Asp Glu Glu Val Phe Gly Pro Leu Leu Arg Val Trp
    370                 375                 380

Arg Tyr Asp Thr Phe Asp Glu Ala Ile Arg Met Ala Asn Asn Thr Arg
385                 390                 395                 400

Phe Gly Leu Ser Cys Gly Leu Val Ser Pro Glu Arg Glu Lys Phe Asp
                405                 410                 415

Gln Leu Leu Leu Glu Ala Arg Ala Gly Ile Val Asn Trp Asn Lys Pro
            420                 425                 430

Leu Thr Gly Ala Ala Ser Thr Ala Pro Phe Gly Gly Ile Gly Ala Ser
        435                 440                 445

Gly Asn His Arg Pro Ser Ala Trp Tyr Ala Ala Asp Tyr Cys Ala Trp
    450                 455                 460

Pro Met Ala Ser Leu Glu Ser Asp Ser Leu Thr Leu Pro Ala Thr Leu
465                 470                 475                 480

Asn Pro Gly Leu Asp Phe Ser Asp Glu Val Val Arg
                485                 490

<210> SEQ ID NO 9
<211> LENGTH: 969
<212> TYPE: DNA
<213> ORGANISM: Escherichia coli
<220> FEATURE:
<221> NAME/KEY: CDS
<222> LOCATION: (1)..(966)

<400> SEQUENCE: 9 atg gat aat ttt ctt gct ctg acc tta acg ggt aaa aaa ccg gtt atc      48
Met Asp Asn Phe Leu Ala Leu Thr Leu Thr Gly Lys Lys Pro Val Ile
1               5                   10                  15 acc gag cga gaa atc aac ggc gtt cgc tgg cgc tgg ctg ggc gat ggt      96
Thr Glu Arg Glu Ile Asn Gly Val Arg Trp Arg Trp Leu Gly Asp Gly
            20                  25                  30
```

| | | |
|---|---|---|
| gtg ctg gaa ctg acg cca tta acg cca ccg caa ggc gca ctg gtg att<br>Val Leu Glu Leu Thr Pro Leu Thr Pro Pro Gln Gly Ala Leu Val Ile<br>            35                    40                        45 | 144 | |
| tca gcg gga ata cac ggt aat gag acg gca cct gtg gag atg ctg gac<br>Ser Ala Gly Ile His Gly Asn Glu Thr Ala Pro Val Glu Met Leu Asp<br>50                    55                        60 | 192 | |

```
gtg ctg gaa ctg acg cca tta acg cca ccg caa ggc gca ctg gtg att     144
Val Leu Glu Leu Thr Pro Leu Thr Pro Pro Gln Gly Ala Leu Val Ile
            35                  40                  45 tca gcg gga ata cac ggt aat gag acg gca cct gtg gag atg ctg gac     192
Ser Ala Gly Ile His Gly Asn Glu Thr Ala Pro Val Glu Met Leu Asp
 50                  55                  60 gcg ttg ctt ggc gcg ata tct cac ggc gag atc ccg tta cgt tgg cgg     240
Ala Leu Leu Gly Ala Ile Ser His Gly Glu Ile Pro Leu Arg Trp Arg
 65                  70                  75                  80 ttg ctg gtg atc ctc ggg aat cct cct gcg ctg aag caa ggg aaa cgt     288
Leu Leu Val Ile Leu Gly Asn Pro Pro Ala Leu Lys Gln Gly Lys Arg
                 85                  90                  95 tat tgc cat agc gat atg aat cga atg ttt ggc ggt cgt tgg cag cta     336
Tyr Cys His Ser Asp Met Asn Arg Met Phe Gly Gly Arg Trp Gln Leu
            100                 105                 110 ttt gct gaa agc gga gaa acc tgt cgg gcg cgc gaa ctg gaa cag tgc     384
Phe Ala Glu Ser Gly Glu Thr Cys Arg Ala Arg Glu Leu Glu Gln Cys
        115                 120                 125 ctg gaa gat ttt tat gac cag ggc aaa gaa tct gtg cgc tgg cac ctt     432
Leu Glu Asp Phe Tyr Asp Gln Gly Lys Glu Ser Val Arg Trp His Leu
    130                 135                 140 gat cta cat acc gca att cgt ggc tcc ttg cat ccg cag ttc ggt gta     480
Asp Leu His Thr Ala Ile Arg Gly Ser Leu His Pro Gln Phe Gly Val
145                 150                 155                 160 tta ccg caa cgc gac att ccc tgg gac gag aaa ttt ctg acg tgg ctg     528
Leu Pro Gln Arg Asp Ile Pro Trp Asp Glu Lys Phe Leu Thr Trp Leu
                165                 170                 175 ggt gcg gcg ggg ctg gag gcg ctg gtg ttc cat cag gaa cct ggt ggt     576
Gly Ala Ala Gly Leu Glu Ala Leu Val Phe His Gln Glu Pro Gly Gly
            180                 185                 190 acg ttt acc cat ttc agc gcc aga cat ttt ggc gcg ctg gcc tgt acg     624
Thr Phe Thr His Phe Ser Ala Arg His Phe Gly Ala Leu Ala Cys Thr
        195                 200                 205 ctg gaa ctt ggc aaa gcg ttg ccc ttt ggg caa aac gat ctt cgc cag     672
Leu Glu Leu Gly Lys Ala Leu Pro Phe Gly Gln Asn Asp Leu Arg Gln
    210                 215                 220 ttt gca gta act gcc agc gca att gct gcg ctg cta tct ggt gag agt     720
Phe Ala Val Thr Ala Ser Ala Ile Ala Ala Leu Leu Ser Gly Glu Ser
225                 230                 235                 240 gtc ggt atc gtg aga aca ccg ccg ctc cgt tat cgg gtg gtt tcg caa     768
Val Gly Ile Val Arg Thr Pro Pro Leu Arg Tyr Arg Val Val Ser Gln
                245                 250                 255 att act cgc cac tcg ccg tcc ttc gaa atg cat atg gca agt gac acg     816
Ile Thr Arg His Ser Pro Ser Phe Glu Met His Met Ala Ser Asp Thr
            260                 265                 270 ctg aat ttt atg ccg ttt gag aaa gga aca ttg ctg gcg cag gac gga     864
Leu Asn Phe Met Pro Phe Glu Lys Gly Thr Leu Leu Ala Gln Asp Gly
        275                 280                 285 gag gaa cgt ttt acc gta acc cat gat gta gag tat gtg tta ttc cct     912
Glu Glu Arg Phe Thr Val Thr His Asp Val Glu Tyr Val Leu Phe Pro
    290                 295                 300 aat ccg ttg gta gcg ttg gga tta cgc gcg gga tta atg ctc gaa aaa     960
Asn Pro Leu Val Ala Leu Gly Leu Arg Ala Gly Leu Met Leu Glu Lys
305                 310                 315                 320 ata agc taa                                                         969
Ile Ser

<210> SEQ ID NO 10
<211> LENGTH: 322
```

<212> TYPE: PRT
<213> ORGANISM: Escherichia coli

<400> SEQUENCE: 10

```
Met Asp Asn Phe Leu Ala Leu Thr Leu Thr Gly Lys Lys Pro Val Ile
1               5                   10                  15

Thr Glu Arg Glu Ile Asn Gly Val Arg Trp Arg Trp Leu Gly Asp Gly
            20                  25                  30

Val Leu Glu Leu Thr Pro Leu Thr Pro Pro Gln Gly Ala Leu Val Ile
        35                  40                  45

Ser Ala Gly Ile His Gly Asn Glu Thr Ala Pro Val Glu Met Leu Asp
    50                  55                  60

Ala Leu Leu Gly Ala Ile Ser His Gly Glu Ile Pro Leu Arg Trp Arg
65                  70                  75                  80

Leu Leu Val Ile Leu Gly Asn Pro Pro Ala Leu Lys Gln Gly Lys Arg
                85                  90                  95

Tyr Cys His Ser Asp Met Asn Arg Met Phe Gly Gly Arg Trp Gln Leu
            100                 105                 110

Phe Ala Glu Ser Gly Glu Thr Cys Arg Ala Arg Glu Leu Glu Gln Cys
        115                 120                 125

Leu Glu Asp Phe Tyr Asp Gln Gly Lys Glu Ser Val Arg Trp His Leu
    130                 135                 140

Asp Leu His Thr Ala Ile Arg Gly Ser Leu His Pro Gln Phe Gly Val
145                 150                 155                 160

Leu Pro Gln Arg Asp Ile Pro Trp Asp Glu Lys Phe Leu Thr Trp Leu
                165                 170                 175

Gly Ala Ala Gly Leu Glu Ala Leu Val Phe His Gln Glu Pro Gly Gly
            180                 185                 190

Thr Phe Thr His Phe Ser Ala Arg His Phe Gly Ala Leu Ala Cys Thr
        195                 200                 205

Leu Glu Leu Gly Lys Ala Leu Pro Phe Gly Gln Asn Asp Leu Arg Gln
    210                 215                 220

Phe Ala Val Thr Ala Ser Ala Ile Ala Ala Leu Leu Ser Gly Glu Ser
225                 230                 235                 240

Val Gly Ile Val Arg Thr Pro Pro Leu Arg Tyr Arg Val Val Ser Gln
                245                 250                 255

Ile Thr Arg His Ser Pro Ser Phe Glu Met His Met Ala Ser Asp Thr
            260                 265                 270

Leu Asn Phe Met Pro Phe Glu Lys Gly Thr Leu Leu Ala Gln Asp Gly
        275                 280                 285

Glu Glu Arg Phe Thr Val Thr His Asp Val Glu Tyr Val Leu Phe Pro
    290                 295                 300

Asn Pro Leu Val Ala Leu Gly Leu Arg Ala Gly Leu Met Leu Glu Lys
305                 310                 315                 320

Ile Ser
```

<210> SEQ ID NO 11
<211> LENGTH: 80
<212> TYPE: DNA
<213> ORGANISM: Artificial Sequence
<220> FEATURE:
<223> OTHER INFORMATION: primer for disrupting astA

<400> SEQUENCE: 11
atggtcatcc gtcccgttga gcgatcagat gtctcggcgc tctagacgct caagttagta    60

-continued

```
taaaaaagct gaacgagaaa                                                        80

<210> SEQ ID NO 12
<211> LENGTH: 80
<212> TYPE: DNA
<213> ORGANISM: Artificial Sequence
<220> FEATURE:
<223> OTHER INFORMATION: primer for disrupting astA

<400> SEQUENCE: 12
aacgctcggt tgccggatcg gtacgcacca gcaccacgcg agatcttgaa gcctgctttt        60
ttatactaag ttggcattat                                                        80
```

METHOD FOR PRODUCING AN L-AMINO ACID IN A CULTURED BACTERIUM HAVING REDUCED ACTIVITY OF THE ARGININE SUCCINYLTRANSFERASE PATHWAY

This application is a Continuation of, and claims priority under 35 U.S.C. §120 to, International Application No. PCT/JP2010/061268, filed Jul. 1, 2010, and claims priority therethrough under 35 U.S.C. §119 to Japanese Patent Application No. 2009-197575, filed Aug. 28, 2009, the entireties of which are incorporated by reference herein. Also, the Sequence Listing filed electronically herewith is hereby incorporated by reference (File name: 2012-02-24T_US-476_Seq_List; File size: 46 KB; Date recorded: Feb. 24, 2012).

BACKGROUND OF THE INVENTION

1. Field of the Invention

The present invention relates to a method for producing an L-amino acid using a microorganism. L-amino acids are useful in various fields, such as ingredients in seasonings, food additives, feed additives, chemicals, and drugs.

2. Brief Description of the Related Art

L-Amino acids are industrially produced by fermentation using microorganisms belonging to the genus *Brevibacterium*, *Corynebacterium*, *Escherichia*, or the like. In such production methods, strains are used which are isolated from nature or artificial variants of such strains. Furthermore, microorganisms modified by recombinant DNA techniques so that activity of a basic L-amino acid biosynthesis enzyme is increased, and so forth are used (EP 0643135 B, EP 0733712 B, EP 1477565 A, EP 0796912 A, EP 0837134 A, WO01/53459, EP 1170376 A, WO2005/010175, WO96/17930).

It has been reported that *Escherichia coli* has a metabolic pathway called the arginine succinyltransferase pathway which acts to decompose L-arginine; 97% of L-arginine decomposition occurs via this arginine succinyltransferase pathway (J. Bacteriol. (1998) Vol. 180, No. 16, 4278-4286). Moreover, it has also been reported that this arginine succinyltransferase pathway decomposes L-arginine with a group of enzymes encoded by the astCADBE operon contained in the genomic sequence of *Escherichia coli* (GenBank Accession No. U00096) (J. Bacteriol., 1998, Vol. 180, No. 16, 4278-4286).

However, the relation between the arginine succinyltransferase pathway and L-amino acid production has not been previously reported.

SUMMARY OF THE INVENTION

An aspect of the present invention is to provide an improved method for producing an L-amino acid by fermentation as compared to conventional methods.

It was found that L-amino acid-producing abilities of Enterobacteriaceae bacteria could be markedly improved by decreasing activity or activities of one or two or more kinds of enzymes of the arginine succinyltransferase pathway.

It is an aspect of the present invention to provide a method for producing an L-amino acid, which comprises culturing a bacterium belonging to the family Enterobacteriaceae and having an L-amino acid-producing ability in a medium to produce and accumulate an L-amino acid in the medium and collecting the L-amino acid from the medium, wherein the bacterium has been modified so that an activity or activities of one or more enzymes of the arginine succinyltransferase pathway is/are decreased.

It is a further aspect of the present invention to provide the method as described above, wherein the enzyme of the arginine succinyltransferase pathway is selected from the group consisting of arginine succinyltransferase, succinylarginine dihydrolase, succinylornithine aminotransferase, succinylglutamate-semialdehyde dehydrogenase, succinylglutamate desuccinylase, and combinations thereof.

It is a further aspect of the present invention to provide the method as described above, wherein the arginine succinyltransferase, succinylarginine dihydrolase, succinylornithine aminotransferase, succinylglutamate-semialdehyde dehydrogenase, and succinylglutamate desuccinylase are encoded by astA, astB, astC, astD, and astE genes, respectively.

It is a further aspect of the present invention to provide the method as described above, wherein the activity or activities of the enzymes of the arginine succinyltransferase pathway is/are decreased by decreasing expression of the gene(s), or by disrupting the gene(s).

It is a further aspect of the present invention to provide the method as described above, wherein the bacterium has been modified so that at least the arginine succinyltransferase activity is decreased.

It is a further aspect of the present invention to provide the method as described above, wherein the bacterium is of a genus selected from the group consisting of *Escherichia*, *Enterobacter*, and *Pantoea*.

It is a further aspect of the present invention to provide the method as described above, wherein the bacterium is *Escherichia coli*.

It is a further aspect of the present invention to provide the method as described above, wherein the L-amino acid is an amino acid of the aspartic acid family or an aromatic amino acid.

It is a further aspect of the present invention to provide the method as described above, wherein the amino acid of the aspartic acid family is selected from the group consisting of L-lysine, L-threonine, L-methionine, and combinations thereof.

It is a further aspect of the present invention to provide the method as described above, wherein the aromatic amino acid is an amino acid selected from the group consisting of L-tryptophan, L-tyrosine, L-phenylalanine, and combinations thereof.

It is a further aspect of the present invention to provide the method as described above, wherein the L-amino acid is L-lysine.

It is a further aspect of the present invention to provide the method as described above, wherein the medium comprises a fatty acid or glycerol as a carbon source.

DETAILED DESCRIPTION OF EXEMPLARY EMBODIMENTS

<1> Bacterium

The bacterium used in the presently disclosed subject matter is a bacterium belonging to the family Enterobacteriaceae and having an L-amino acid producing ability, which has been modified so that an activity or activities of one or two or more kinds of enzymes of the arginine succinyltransferase pathway (henceforth also referred to "AST pathway") is/are decreased. The bacterium can be obtained by modifying a bacterium belonging to the family Enterobacteriaceae and having an L-amino acid-producing ability so that an activity of an enzyme of the AST pathway is decreased.

Bacteria used as a parent strain of the bacterium of the presently disclosed subject matter, which is modified so that an activity of an enzyme of the AST pathway is decreased, and methods for imparting or enhancing an L-amino acid-producing ability is exemplified below. The bacterium can also be obtained by imparting an L-amino acid-producing ability to a bacterium which belongs to the family Enterobacteriaceae and has been modified so that an activity of an enzyme of the AST pathway is decreased, or by enhancing an L-amino acid-producing ability of a bacterium which belongs to the family Enterobacteriaceae and has been modified so that an activity of an enzyme of the AST pathway is decreased.

The bacterium having an amino acid-producing ability refers to a bacterium having an ability to produce and accumulate an L-amino acid in a medium when it is cultured in the medium, for example, such a bacterium that can accumulate the objective L-amino acid in the medium in an amount of 0.5 g/L or more, or 1.0 g/L or more.

Examples of the L-amino acid include L-lysine, L-glutamic acid, L-threonine, L-valine, L-leucine, L-isoleucine, L-serine, L-asparatic acid, L-asparagine, L-glutamine, L-arginine, L-cysteine (cystine), L-methionine, L-phenylalanine, L-tryptophan, L-tyrosine, L-glycine, L-alanine, L-proline, L-ornithine, L-citrulline, and L-homoserine. An amino acid of the aspartic acid family or an aromatic amino acid are particular examples. Examples of the amino acids of the aspartic acid family include L-lysine, L-threonine, and L-methionine. Examples of the aromatic amino acid include L-tryptophan, L-phenylalanine, and L-tyrosine.

In addition, the L-amino acid include not only those in a free form, but also salts thereof including sulfates, hydrochlorides, carbonates, ammonium salts, sodium salts, and potassium salts.

<1-1> Bacteria Used as Parent Strain

The bacterium of the presently disclosed subject matter is a bacterium belonging to the family Enterobacteriaceae and having an L-amino acid-producing ability.

The family Enterobacteriaceae encompasses bacteria belonging to the genera of *Escherichia, Enterobacter, Erwinia, Klebsiella, Pantoea, Photorhabdus, Providencia, Salmonella, Serratia, Shigella, Morganella, Yersinia*, and so forth. In particular, bacteria classified into the family Enterobacteriaceae according to the taxonomy used in the NCBI (National Center for Biotechnology Information) database (www.ncbi.nlm.nih.gov/Taxonomy/Browser/wwwtax.cgi?id=91347) can be used.

The expression "a bacterium belonging to the genus *Escherichia*" means that the bacterium is classified into the genus *Escherichia* according to classification known to a person skilled in the art of microbiology, although the bacterium is not particularly limited. Examples of the bacterium belonging to the genus *Escherichia* include, but are not limited to, *Escherichia coli* (*E. coli*).

The bacterium belonging to the genus *Escherichia* is not particularly limited. However, examples include, for example, the bacteria of the phyletic groups described in the work of Neidhardt et al. (Neidhardt F. C. Ed., 1996, *Escherichia coli* and *Salmonella*: Cellular and Molecular Biology/Second Edition, pp. 2477-2483, Table 1, American Society for Microbiology Press, Washington, D.C.). Specific examples include the *Escherichia coli* W3110 (ATCC 27325), *Escherichia coli* MG1655 (ATCC 47076) and so forth derived from the prototype wild-type strain, K12 strain.

These strains are available from, for example, American Type Culture Collection (Address: P.O. Box 1549 Manassas, Va. 20108, United States of America). That is, accession numbers are given to each of the strains, and the strains can be ordered by using these numbers. The accession numbers of the strains are listed in the catalogue of the American Type Culture Collection.

The expression "a bacterium belonging to the genus *Pantoea*" means that the bacterium is classified into the genus *Pantoea* according to classification known to a person skilled in the art of microbiology. Some strains of *Enterobacter agglomerans* have been recently re-classified into *Pantoea agglomerans, Pantoea ananatis, Pantoea stewartii* or the like on the basis of the nucleotide sequence analysis of 16S rRNA etc. (Int. J. Syst. Bacteriol., 1993, 43, 162-173). Bacteria belonging to the genus *Pantoea* can encompass such bacteria re-classified into the genus *Pantoea* as described above.

Methods for imparting an L-amino acid-producing ability to such bacteria as described above and methods for enhancing an L-amino acid-producing ability of such bacteria as described above are described below.

To impart an L-amino acid-producing ability, methods conventionally employed in the breeding of amino acid-producing strains of coryneform bacteria, *Escherichia* bacteria, and so forth (see "Amino Acid Fermentation", Gakkai Shuppan Center (Ltd.), 1st Edition, published May 30, 1986, pp. 77-100) can be used. Such methods include acquiring an auxotrophic mutant strain, an L-amino acid analogue-resistant strain, or a metabolic regulation mutant strain, or constructing a recombinant strain so that it overexpresses an L-amino acid biosynthesis enzyme. In the breeding of L-amino acid-producing bacteria, one or more of the above-described properties such as auxotrophy, analogue resistance, and metabolic regulation mutation can be imparted. Expression of one or two or more kinds of L-amino acid biosynthesis enzymes can be enhanced. Furthermore, impartation of such properties as auxotrophy, analogue resistance, and metabolic regulation mutation can be combined with enhancement of a biosynthesis enzyme.

An auxotrophic mutant strain, L-amino acid analogue-resistant strain, or metabolic regulation mutant strain having an L-amino acid-producing ability can be obtained by subjecting a parent or wild-type strain to conventional mutatagenesis, such as exposure to X-rays or UV irradiation or a treatment with a mutagen such as N-methyl-N'-nitro-N-nitrosoguanidine, and then selecting a strain exhibiting autotrophy, analogue resistance or a metabolic regulation mutation and having an L-amino acid-producing ability from the obtained mutant strains.

Moreover, the L-amino acid-producing ability can also be imparted or enhanced by increasing an enzymatic activity by gene recombination. An example of the method for increasing enzymatic activity includes modifying the bacterium so that expression of a gene coding for an enzyme involved in biosynthesis of an L-amino acid is enhanced. Expression of a gene can also be increased by introducing an amplification plasmid prepared by introducing a DNA fragment containing the gene into an appropriate plasmid, for example, a plasmid vector containing at least a gene responsible for replication and proliferation of the plasmid in microorganisms, increasing copy number of the gene on a chromosome by conjugation, transfer, or the like, or introducing a mutation into promoter region of the gene (refer to WO95/34672). Furthermore, activity of an enzyme that catalyzes a reaction for generating a compound other than the objective L-amino acid by branching off from the biosynthetic pathway of the objective L-amino acid may be decreased or eliminated. The activity of the enzyme can be decreased or eliminated in the same manner as that for decreasing an activity of an enzyme of the arginine succinyltransferase pathway described below.

When an objective gene is introduced into the aforementioned amplification plasmid or chromosome, any promoter can be used to express the gene so long as the chosen promoter functions in Enterobacteriaceae bacteria. The promoter may be a native promoter for the gene, or a modified promoter. Expression of a gene can also be controlled by suitably choosing a promoter that strongly functions in Enterobacteriaceae bacteria, or by making the −35 and −10 regions of the promoter closer to the consensus sequence. These methods for enhancing expression of enzyme genes are described in WO00/18935, EP 1010755 A, and so forth.

Specific methods for imparting an L-amino acid-producing ability to bacteria and bacteria imparted with L-amino acid-producing ability are exemplified below.

L-Threonine-Producing Bacteria

Examples of microorganisms having L-threonine-producing ability include bacteria in which one or more activities of L-threonine biosynthetic enzymes are enhanced. Examples of L-threonine biosynthetic enzymes include aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). The names of the genes coding for the respective enzymes are mentioned in the parentheses after the names of the enzymes (the same shall apply throughout this specification). In a particular example, aspartate semialdehyde dehydrogenase, aspartokinase I, homoserine kinase, aspartate aminotransferase, or threonine synthase can be used. The genes coding for the L-threonine biosynthetic enzymes can be introduced into an *Escherichia* bacterium which has a decreased ability to decompose threonine. Examples of such an *Escherichia* bacterium having a decreased ability to decompose threonine include the TDH6 strain which is deficient in the threonine dehydrogenase activity (Japanese Patent Laid-open No. 2001-346578), and so forth.

The enzymatic activities of the L-threonine biosynthetic enzymes are inhibited by the endproduct, L-threonine. Therefore, for construction of L-threonine-producing strains, genes of the L-threonine biosynthetic enzymes can be modified so that the enzymes are desensitized to the feedback inhibition by L-threonine. The aforementioned thrA, thrB, and thrC genes constitute the threonine operon, which contains an attenuator structure. The expression of the threonine operon is inhibited by isoleucine and threonine in the culture medium and also suppressed by attenuation. Therefore, the above-mentioned modification can be attained by removing the leader sequence or attenuator in the attenuation region (refer to Lynn, S. P., Burton, W. S., Donohue, T. J., Gould, R. M., Gumport, R. L, and Gardner, J. F., J. Mol. Biol. 194:59-69 (1987); WO02/26993; WO2005/049808).

The native promoter of the threonine operon is present upstream of the threonine operon. It may be replaced with a non-native promoter (refer to WO98/04715), or a threonine operon which has been modified so that expression of a threonine biosynthesis gene is controlled by the repressor and promoter of 2-phage may be constructed (EP 0593792 B). Furthermore, in order to modify a bacterium so that it is desensitized to feedback inhibition by L-threonine, a strain resistant to α-amino-β-hydroxyisovaleric acid (AHV) can be selected.

Copy number of the threonine operon that is modified to desensitize to feedback inhibition by L-threonine as described above can be increased in a host, or expression of the threonine operon can be increased by ligating it to a potent promoter. The copy number can be increased by, besides amplification using a plasmid, transferring the threonine operon to a genome using a transposon, Mu-phage, or the like.

Other than increasing expression of the L-threonine biosynthetic enzyme genes, expression of the genes involved in the glycolytic pathway, TCA cycle, or respiratory chain, the genes that regulate the expression of these genes, or the genes involved in sugar uptake can also be increased. Examples of such genes effective on the threonine production include the transhydrogenase gene (pntAB, EP 733712 B), phosphoenolpyruvate carboxylase gene (pepC, WO95/06114), phosphoenolpyruvate synthase gene (pps, EP 877090 B), and a pyruvate carboxylase gene of coryneform bacterium or *Bacillus* bacterium (WO99/18228, EP 1092776 A).

Expression of a gene that imparts resistance to L-threonine or resistance to L-homoserine can be enhanced, or resistance to L-threonine or resistance to L-homoserine to the host can be imparted. Examples of genes that imparts such resisitance include rhtA (Res. Microbiol., 154:123-135 (2003)), rhtB (EP 0994190 A), rhtC (EP 1013765 A), yfiK and yeaS (EP 1016710 A). As for the methods for imparting L-threonine resistance to a host, the methods described in EP 0994190 A and WO90/04636 can be referred to.

Examples of L-threonine-producing bacteria and parent strains which can be used to derive such bacteria include, but are not limited to, strains belonging to the genus *Escherichia*, such as *E. coli* TDH-6/pVIC40 (VKPM B-3996) (U.S. Pat. Nos. 5,175,107 and 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A) and so forth.

The TDH-6 strain is deficient in the thrC gene, as well as being sucrose-assimilative, and the ilvA gene thereof has a leaky mutation. This strain also has a mutation in the rhtA gene, which imparts resistance to high concentration of threonine or homoserine. The B-3996 strain harbors the plasmid pVIC40, which is obtained by inserting the thrA*BC operon containing a mutant thrA gene into the RSF1010-derived vector. This mutant thrA gene codes for aspartokinase homoserine dehydrogenase I which is substantially desensitized to feedback inhibition by threonine. The B-3996 strain was deposited on Nov. 19, 1987 at the All-Union Scientific Center of Antibiotics (Nagatinskaya Street 3-A, 117105 Moscow, Russia) under the accession number RIA 1867. The strain was also deposited at the Russian National Collection of Industrial Microorganisms (VKPM) (1 Dorozhny proezd., 1 Moscow 117545, Russia) on Apr. 7, 1987 under the accession number VKPM B-3996.

*E. coli* VKPM B-5318 (EP 0593792 B) can also be used as an L-threonine-producing bacterium or a parent strain for deriving it. The B-5318 strain is prototrophic with regard to isoleucine, and a temperature-sensitive λ-phage Cl repressor and PR promoter replace the regulatory region of the threonine operon in the plasmid pVIC40. The VKPM B-5318 strain was deposited as an international deposit at the Russian National Collection of Industrial Microorganisms (VKPM) (1 Dorozhny proezd., 1 Moscow 117545, Russia) on May 3, 1990 under the accession number of VKPM B-5318.

The thrA gene coding for aspartokinase homoserine dehydrogenase I of *Escherichia coli* has been elucidated (nucleotide numbers 337 to 2799, GenBank accession NC_000913.2, gi: 49175990). The thrA gene is located between the thrL and thrB genes on the chromosome of *E. coli* K-12. The thrB gene coding for homoserine kinase of

*Escherichia coli* has been elucidated (nucleotide numbers 2801 to 3733, GenBank accession NC 000913.2, gi: 49175990). The thrB gene is located between the thrA and thrC genes on the chromosome of *E. coli* K-12. The thrC gene coding for threonine synthase of *Escherichia coli* has been elucidated (nucleotide numbers 3734 to 5020, GenBank accession NC 000913.2, gi: 49175990). The thrC gene is located between the thrB gene and the yaaX open reading frame on the chromosome of *E. coli* K-12. All three genes function as a single threonine operon. To enhance expression of the threonine operon, the attenuator region that affects the transcription can be removed from the operon (WO2005/049808, WO2003/097839).

A mutant thrA gene coding for aspartokinase homoserine dehydrogenase I resistant to feedback inhibition by threonine, as well as the thrB and thrC genes can be obtained as a single operon from the well-known pVIC40 plasmid, which is present in the threonine-producing *E. coli* strain VKPM B-3996. The plasmid pVIC40 is described in detail in U.S. Pat. No. 5,705,371.

The rhtA gene is present at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181), and is located between the pexB and ompX genes. The unit that expresses the protein encoded by the ORF1 is referred to as rhtA gene (rht: resistant to homoserine and threonine). It was also revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, Abstract No. 457, EP 1013765 A).

The asd gene of *E. coli* has already been elucidated (nucleotide numbers 3572511 to 3571408, GenBank accession NC_0O0913.1, gi:16131307), and can be obtained by PCR (refer to White, T. J. et al., Trends Genet, 5, 185 (1989)) utilizing primers prepared on the basis of the nucleotide sequence of the gene. The asd genes of other microorganisms can also be obtained in a similar manner.

The aspC gene of *E. coli* has also already been elucidated (nucleotide numbers 983742 to 984932, GenBank accession NC 000913.1, gi:16128895), and can be obtained by PCR. The aspC genes of other microorganisms can also be obtained in a similar manner.

L-Lysine-Producing Bacteria

Examples of L-lysine-producing bacteria belonging to the genus *Escherichia* include mutants which are resistant to an L-lysine analogue. L-lysine analogues inhibit the growth of *Escherichia* bacteria, but this inhibition is fully or partially desensitized when L-lysine is present in the medium. Examples of these L-lysine analogues include, but are not limited to, oxalysine, lysine hydroxamate, S-(2-aminoethyl)-L-cysteine (AEC), γ-methyllysine, α-chlorocaprolactam, and so forth. Mutants which are resistant to these lysine analogues can be obtained by subjecting *Escherichia* bacteria to conventional artificial mutagenesis treatments. Specific examples of bacterial strains useful for producing L-lysine include *Escherichia coli* AJ11442 (fERM BP-1543, NRRL B-12185; see U.S. Pat. No. 4,346,170) and *Escherichia coli* VL611. In these microorganisms, feedback inhibition of aspartokinase by L-lysine is desensitized.

Examples of L-lysine-producing bacteria and parent strains that can be used to derive L-lysine-producing bacteria also include strains in which activity or activities of one or more kinds of L-lysine biosynthetic enzymes is/are enhanced. Examples of such enzymes include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenease (asd), diaminopimelate epimerase (dapF), tetrahydrodipicolinate succinylase (dapD), succinyl diaminopimelate deacylase (dapE), and aspartase (aspA) (EP 1253195 A). In a particular example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenease, tetrahydrodipicolinate succinylase, or succinyl diaminopimelate deacylase can be enhanced. In addition, the parent strains can express increased levels of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), which is a gene for L-lysine secretion, or combinations of these.

Examples of L-lysine-producing bacteria and parent strains that can be used to derive L-lysine-producing bacteria also include strains in which activity of an enzyme that catalyzes a reaction for synthesis of a compound other than L-lysine branching away from the biosynthetic pathway of L-lysine is decreased or eliminated. Examples of such an enzyme include homoserine dehydrogenase, lysine decarboxylase (U.S. Pat. No. 5,827,698), and the malic enzyme (WO2005/010175).

Examples of L-lysine-producing strains include *E. coli* WC196ΔcadAΔldcC/pCABD2 (WO2006/078039). This strain was obtained by introducing the pCABD2 plasmid containing lysine biosynthesis enzyme genes (U.S. Pat. No. 6,040,160) into the WC196 strain, in which the cadA and ldcC genes coding for lysine decarboxylase are disrupted. The WC196 strain was bred from the W3110 strain, which was derived from *Escherichia coli* K-12, by replacing the wild-type lysC gene on the chromosome of the W3110 strain with a mutant lysC gene encoding a mutant aspartokinase III desensitized to feedback inhibition by L-lysine in which threonine at position 352 was replaced with isoleucine (U.S. Pat. No. 5,661,012), and conferring AEC resistance to the resulting strain (U.S. Pat. No. 5,827,698). The WC196 strain was designated *Escherichia coli* AJ13069 and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and assigned an accession number of FERM P-14690. Then, the deposit was converted to an international deposit under the provisions of the Budapest Treaty on Sep. 29, 1995, and assigned an accession number of FERM BP-5252 (U.S. Pat. No. 5,827,698). The WC196ΔcadAΔldcC strain per se can be used for L-lysine-producing strain. The WC196ΔcadAΔldcC strain was designated *Escherichia coli* AJ110692 and was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Oct. 7, 2008 as an international deposit under the provisions of the Budapest Treaty and assigned an accession number of FERM BP-11027.

The pCABD2 plasmid contains a mutant dapA gene derived from *Escherichia coli*, which has been mutated to encode dihydrodipicolinate synthase (DDPS) desensitized to the feedback inhibition by L-lysine, a mutant lysC gene derived from *Escherichia coli*, which has been mutated to encode aspartokinase III desensitized to feedback inhibition by L-lysine, the dapB gene derived from *Escherichia coli* coding for dihydrodipicolinate reductase, and the ddh gene derived from *Brevibacterium lactofermentum* coding for diaminopimelate dehydrogenase (WO95/16042, WO01/53459).

L-Methionine-Producing Bacteria

As an L-methionine-producing bacterium, an *Escherichia* bacterium deficient in the repressor (metJ) of the L-methionine biosynthesis system and having an enhanced intracellular homoserine transsuccinylase activity (metA), or having an attenuated S-adenosylmethionine syntase activity (metK) can be used (Japanese Patent No. 04110641).

L-tryptophan, L-phenylalanine, and L-tyrosine are all aromatic amino acids and share a common biosynthesis pathway. Examples of the genes encoding the biosynthetic enzymes for these aromatic amino acids include genes of deoxyarabino-heptulosonate phosphate synthase (aroG), chorismate mutase/prephenate dehydratase (pheA), 3-dehydroquinate synthase (aroB), shikimic acid dehydratase (aroE), shikimate kinase (aroL), 5-enolpyruvylshikimate-3-phosphate synthase (aroA), and chorismate synthase (aroC) (EP 763127 A). It is known that these genes are controlled by the tyrosine repressor (tyrR), and so activity of an aromatic amino acid biosynthetic enzyme may also be increased by deleting the tyrR gene (see EP 763127 B).

Furthermore, 3-deoxy-D-arabinoheptulosonate-7-phosphate synthetase (aroF, aroG) is subject to feedback inhibition by aromatic amino acids. Therefore, the enzyme can be modified so that it is not subject to the feedback inhibition. An aromatic L-amino acid-producing bacterium can be obtained, for example, by introducing a mutant aroF coding for a protein in which the L-aspartic acid at position 147 or the L-serine at position 181, as counted from the N-terminus, is replaced by another amino acid, or by introducing a mutant aroG gene coding for a protein in which the L-aspartic acid at position 146, the L-methionine at position 147, the L-proline at position 150 or the L-alanine at position 202, or both the L-methionine at position 157 and the L-alanine at position 219, as counted from the N-terminus, are replaced by other amino acid(s) (EP 0488424 A). Furthermore, the chorismate mutase/prephenate dehydratase also suffers from feedback inhibition by aromatic amino acids, and it may be modified so as to be desensitized to the feedback inhibition.

The biosynthesis systems of the aromatic amino acids include a common part, and a strain in which a biosynthesis system characteristic to an aromatic amino acid other than the objective L-amino acid is attenuated can be used. For example, a strain that efficiently produces an objective L-amino acid can be obtained by attenuating biosynthesis systems characteristic to L-phenylalanine or L-tyrosine, when the objective amino acid is L-tryptophan, or by attenuating biosynthesis systems characteristic to L-tryptophan or L-tyrosine, when the objective amino acid is L-phenylalanine. Attenuation of a biosynthesis system can be attained by introducing a mutation into a gene coding for an enzyme of the biosynthesis system, or obtaining a strain requiring an L-amino acid synthesized by the biosynthesis system to be attenuated using a synthetic medium containing that L-amino acid (U.S. Pat. No. 4,371,614).

L-Tryptophan-Producing Bacteria

Examples of L-tryptophan-producing bacteria and parent strains which can be used to derive such bacteria include, but are not limited to, strains belonging to the genus *Escherichia*, such as *E. coli* JP4735/pMU3028 (DSM10122) and JP6015/pMU91 (DSM10123) deficient in tryptophanyl-tRNA synthetase encoded by a mutant trpS gene (U.S. Pat. No. 5,756,345), *E. coli* AGX17 (pGX44) (NRRL B-12263) and AGX6 (pGX50)aroP (NRRL B-12264) deficient in tryptophanase (U.S. Pat. No. 4,371,614), *E. coli* AGX17/pGX50, pACKG4-pps in which a phosphoenolpyruvate-producing ability is enhanced (WO97/08333, U.S. Pat. No. 6,319,696), and so forth. L-tryptophan-producing bacteria belonging to the genus *Escherichia* having enhanced activity of the protein encoded by the yedA or yddG gene may also be used (U.S. Patent Published Application Nos. 2003/0148473 A1 and 2003/0157667 A1).

Examples of L-tryptophan-producing bacteria and parent strains which can be used to derive such bacteria also include strains in which one or more activities of the following enzymes are enhanced: anthranilate synthase (trpE), phosphoglycerate dehydrogenase (serA), 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), chorismate synthase (aroC), prephenate dehydratase, chorismate mutase, and tryptophan synthase (trpAB) and tryptophan synthase (trpAB). The anthranilate synthase and phosphoglycerate dehydrogenase are both suffer from feedback inhibition by L-tryptophan and L-serine, and therefore a mutation desensitizing the feedback inhibition may be introduced into these enzymes. Specific examples of strains having such a mutation include *E. coli* SV164 which harbors desensitized anthranilate synthase and a transformant strain SV164(pGH5) obtained by introducing into the *E. coli* SV164 the plasmid pGH5, which contains a mutant serA gene encoding feedback inhibition-desensitized phosphoglycerate dehydrogenase.

The aforementioned *E. coli* SV164(trpE8) is a strain obtained by introducing a mutant trpE gene coding for anthranilate synthase desensitized to the feedback inhibition by L-tryptophan into a trpE deficient strain, *Escherichia coli* KB862 (DSM7196) (WO94/08031, Japanese Patent Laid-open No. 7-507693). The *E. coli* SV164(pGH5) strain is a strain obtained by introducing a plasmid pGH5 (WO94/08031) containing a mutant serA5 gene coding for phosphoglycerate dehydrogenase desensitized to the feedback inhibition by serine into the SV164 strain. The *E. coli* SV164 (pGH5) strain produces not only L-tryptophan but also L-serine (U.S. Pat. No. 7,045,320).

The aforementioned *E. coli* KB862 strain was designated AJ13828 and was deposited on Dec. 21, 2000 at National Institute of Bioscience and Human Technology of Agency of Industrial Science and Technology (currently independent administrative agency, National Institute of Advanced Industrial Science and Technology, International Patent Organism Depositary, Tsukuba Central 6, 1-1, Higashi 1-Chome, Tsukuba-shi, Ibaraki-ken, 305-8566, Japan) as an international deposit under the provisions of the Budapest Treaty, and assigned an accession number of FERM BP-7405.

Examples of L-tryptophan-producing bacteria and parent strains which can be used to derive such bacteria also include a strain which has enhanced activity of 3-phosphoserine phosphatase (serB) (U.S. Pat. No. 4,371,614), a strain which has enhanced activity of phosphoenolpyruvate carboxykinase (pckA) (WO2004/090125), and a strain which constitutively express maleate synthase-isocitrate lyase-isocitrate dehydrogenase-kinase/phosphatase operon (ace operon), or of which expression of this operon is enhanced (WO2005/103275).

Examples of L-tryptophan-producing bacteria and parent strains which can be used to derive such bacteria also include strains which have been transformed with the tryptophan operon containing a gene encoding inhibition-desensitized anthranilate synthase (Japanese Patent Laid-open Nos. 57-71397, 62-244382, U.S. Pat. No. 4,371,614). Moreover, L-tryptophan-producing ability may be imparted by enhancing expression of a gene coding for tryptophan synthase in the tryptophan operon (trpBA). Tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Phenylalanine-Producing Bacteria

Examples of L-phenylalanine-producing bacteria and parent strains which can be used to derive such bacteria include, but are not limited to, strains belonging to the genus *Escherichia*, such as *E. coli* AJ12479 (FERM BP-4796) (EP 1484410 A), *E. coli* AJ12739 deficient in chorismate mutase/prephenate dehydratase and tyrocine repressor (tyrA::Tn10, tyrR) (VKPM B-8197), *E. coli* HW1089 (ATCC 55371) harboring a mutant pheA34 gene coding for chorismate mutase-prephenate dehydratase desensitized to feedback inhibition (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952). As a parent strain, *E. coli* K-12 [W3110 (tyrA)/pPHAB] (FERM BP-3566) harboring a gene coding for chorismate mutase-prephenate dehydratase desensitized to feedback inhibition, *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ12604 (FERM BP-3579) can also be used (EP 488424 B1). Furthermore, L-phenylalanine-producing bacteria belonging to the genus *Escherichia* with an enhanced activity of the protein encoded by the yedA gene or the yddG gene may also be used (U.S. Patent Published Application Nos. 2003/0148473 A1 and 2003/0157667 A1).

As for phenylalanine-producing bacteria, by such modification that bacteria incorporate by-products into cells, for example, by increasing expression of the L-tryptophan uptake gene, tnaB or mtr, or the L-tyrosine uptake gene, tyrP, strains efficiently producing L-phenylalanine can also be obtained (EP 1484410).

L-Tyrosine-Producing Bacteria

Examples of tyrosine-producing bacteria include *Escherichia* bacteria having a desensitized type prephenate dehydratase gene (tyrA), the product of which is not inhibited by tyrosine (EP 1616940 A).

When the bacterium is bred by gene recombination, the genes to be used are not limited to genes having the genetic information described above or genes having known sequences, but also include variants of the genes, namely, genes having conservative mutations, such as homologues of the genes or artificially modified genes, can also be used so long as the functions of the encoded proteins are not degraded. That is, they may be genes encoding a known amino acid sequence containing one or more substitutions, deletions, insertions, additions or the like of one or several amino acid residues at one or several positions.

Although the number of the "one or several" amino acid residues referred to herein may differ depending on the position in the three-dimensional structure of the protein or the types of amino acid residues, specifically, it may be 1 to 20, 1 to 10, or 1 to 5. The conservative mutation is typically a conservative substitution. The conservative substitution is a mutation wherein substitution takes place mutually among Phe, Trp, and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitutions, deletions, insertions, additions, inversions or the like may be a result of a naturally-occurring mutation or a variation due to an individual difference or difference of species of a microorganism from which the genes are derived (mutant or variant). Such genes can be obtained by, for example, modifying a known nucleotide sequence of a gene by site-specific mutagenesis so that the amino acid residues at the specific sites of the encoded protein include substitutions, deletions, insertions, or additions of amino acid residues.

Furthermore, such genes having conservative mutation(s) as described above may encode a protein having a homology of 80% or more, 90% or more, 95% or more, or 97% or more, to the entire encoded amino acid sequence and having a function equivalent to that of the wild-type protein.

Moreover, codons in the gene sequences may be replaced with other codons which are easily used in the host into which the genes are introduced.

The genes having conservative mutation(s) may be obtained by methods usually used in mutagenesis treatments such as treatments with mutagenesis agents.

Furthermore, the genes may be a DNA which can hybridize with a complementary sequence of a known gene sequence or a probe which can be prepared from such a complementary sequence under stringent conditions and encodes a protein having a function equivalent to that of the known gene product. The "stringent conditions" can be conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, or not less than 97% homologous, hybridize to each other, and DNAs less homologous than the above do not hybridize to each other, or conditions of washing once, or 2 or 3 times, at a salt concentration and temperature corresponding to washing typical of Southern hybridization, i.e., 1×SSC, 0.1% SDS at 60° C., 0.1×SSC, 0.1% SDS at 60° C., or 0.1×SSC, 0.1% SDS at 68° C.

As the probe, a part of a complementary sequence of a gene can also be used. Such a probe can be prepared by PCR using oligonucleotides prepared on the basis of a known gene sequence as primers and a DNA fragment containing the nucleotide sequences as a template. For example, when a DNA fragment having a length of about 300 bp is used as the probe, the washing conditions of hybridization may be 50° C., 2×SSC and 0.1% SDS.

The aforementioned descriptions concerning variants of genes are similarly applied to the genes coding for the enzymes of the arginine succinyltransferase pathway described below and the other genes mentioned in this specification.

The bacterium may be any bacterium so long as a bacterium that can assimilate a saccharide used for usual amino acid fermentation, such as glucose and sucrose, is chosen. However, a bacterium can have an ability to assimilate glycerol or a fatty acid, and the bacterium may be a bacterium inherently having an ability to assimilate glycerol or a fatty acid, a recombinant strain imparted with an ability to assimilate glycerol or a fatty acid, or a mutant strain of which ability to assimilate glycerol or a fatty acid is enhanced.

The L-amino acid-producing bacterium may be modified so that an ability to assimilate glycerol is enhanced. The ability to assimilate glycerol can be enhanced by modifying a gene involved in the glycerol metabolism.

As for genes involved in the glycerol metabolism, in order to enhance glycerol-assimilating ability, expression of the glpR gene (EP 1715056) may be attenuated, or expression of the glycerol metabolism genes (EP 1715055 A) such as glpA, glpB, glpC, glpD, glpE, glpF, glpG, glpK, glpQ, glpT, glpX, tpiA, gldA, dhaK, dhaL, dhaM, dhaR, fsa, and talC genes may be enhanced. In particular, in order to enhance glycerol-assimilating ability, expressions of the glycerol dehydrogenase gene (gldA), dihydroxyacetone kinase gene (dhaKLM, dak), and fructose-6-phosphate aldolase gene (fsaB) can be enhanced (WO2008/102861).

Furthermore, as for glycerol kinase (glpK), a glpK gene encoding a mutant glycerol kinase which is not subject to the feedback inhibition by fructose-1,6-phosphate can be used (WO2008/081959, WO2008/107277)

The L-amino acid-producing bacterium may be modified so that an ability to assimilate a hydrolysate of fats and oils or a fatty acid is increased. Examples of such modification include, for example, deletion of the gene coding for the transcription factor FadR having a DNA-binding ability that controls the fatty acid metabolism which is found in the Enterobacteriaceae bacteria (DiRusso, C. C. et al., 1992, J. Biol. Chem., 267:8685-8691; DiRusso, C. C. et al., 1993, Mol. Microbiol., 7:311-322). Specifically, the fadR gene of *Escherichia coli* is, for example, a gene located at the nucleotide numbers 1,234,161 to 1,234,880 of the genomic sequence of *Escherichia coli* MG1655 strain registered with Genbank Accession No. U00096, and coding for the protein registered with GenBank Accession No. AAC74271.

In order to enhance the ability to assimilate a hydrolysate of fats and oils or a fatty acid, expression of one or more of genes selected from fadA, fadB, fadI, fadJ, fadL, fadE and fadD may be enhanced.

The "fadL gene" can mean a gene encoding a transporter of the outer membrane having an ability to take up a long chain fatty acid, which is found in the Enterobacteriaceae bacteria (Kumar, G. B. and Black, P. N., 1993, J. Biol. Chem., 268: 15469-15476; Stenberg, F. et al., 2005, J. Biol. Chem., 280: 34409-34419). Specific examples of a gene encoding FadL include the gene located at the nucleotide numbers 2459322 to 2460668 of the *Escherichia coli* genomic sequence (Genbank Accession No. U00096) as the fadL gene of *Escherichia coli*.

The "fadD gene" can mean a gene coding for an enzyme having the fatty acyl-CoA synthetase activity, which generates a fatty acyl-CoA from a long chain fatty acid, and taking up it through the inner membrane, and which is found in the Enterobacteriaceae bacteria (Dirusso, C. C. and Black, P. N., 2004, J. Biol. Chem., 279:49563-49566; Schmelter, T. et al., 2004, J. Biol. Chem., 279: 24163-24170). Specific examples of a gene encoding FadD include the gene located at the nucleotide numbers 1887770 to 1886085 (complementary strand) of the *Escherichia coli* genomic sequence (GenBank Accession No. U00096) as the fadD gene of *Escherichia coli*.

The "fadE gene" can mean a gene encoding an enzyme having the acyl-CoA dehydrogenase activity for oxidizing a fatty acyl-CoA, which is found in the Enterobacteriaceae bacteria (O'Brien, W. J. and Frerman, E E. 1977, J. Bacteriol., 132:532-540; Campbell, J. W. and Cronan, J. E., 2002, J. Bacteriol., 184:3759-3764).

Specific examples of a gene coding for FadE include the gene located at the nucleotide numbers 243303 to 240859 (complementary strand) of the *Escherichia coli* genomic sequence (GenBank Accession No. U00096) and having the nucleotide sequence shown in SEQ ID NO: 7 as the fadE gene of *Escherichia coli*. The amino acid sequence encoded by this gene is shown in SEQ ID NO: 8.

The "fadB gene" can mean a gene coding for an enzyme constituting the α component of a fatty acid oxidation complex found in the Enterobacteriaceae bacteria and having four kinds of activities of enoyl-CoA hydratase, 3-hydroxyacyl-CoA dehydrogenase, 3-hydroxyacyl-CoA epimerase and Δ3-cis-Δ2-trans-enoyl-CoA isomerase (Pramanik, A. et al., 1979, J. Bacteriol., 137:469-473; Yang, S. Y. and Schulz, H., 1983, J. Biol. Chem., 258:9780-9785). Specific examples of a gene coding for FadB include the gene located at the nucleotide numbers 4028994 to 4026805 (complementary strand) of the *Escherichia coli* genomic sequence (GenBank Accession No. U00096) as the fadB gene of *Escherichia coli*.

The "fadA gene" can mean a gene coding for an enzyme constituting the β component of the fatty acid oxidation complex found in the Enterobacteriaceae bacteria and having the 3-ketoacyl-CoA thiolase activity (Pramanik, A. et al., 1979, J. Bacteriol., 137: 469-473). Specific examples of a gene coding for FadA include the gene located at the nucleotide numbers 4026795 to 4025632 (complementary strand) of the *Escherichia coli* genomic sequence (GenBank Accession No. U00096) as the fadA gene of *Escherichia coli*.

It is known that FadB and FadA form a complex in the fatty acid oxidation complex found in the Enterobacteriaceae bacteria, and the genes also form the fadBA operon (Yang, S. Y. et al., 1990, J. Biol. Chem., 265:10424-10429). Therefore, the entire operon can also be amplified as the fadBA operon.

The ability to assimilate a hydrolysate of fats and oils or a fatty acid can also be enhanced by enhancing the cyo operon (cyoABCDE). The "cyoABCDE" can mean a group of genes coding for the subunits of the cytochrome bo type oxidase complex as one of the terminal oxidases found in the Enterobacteriaceae bacteria. The cyoB codes for the subunit I, cyoA codes for the subunit II, cyoC codes for the subunit III, cyoD codes for the subunit IV, and cyoE codes for an enzyme showing the heme O synthase activity (Gennis, R. B. and Stewart, V., 1996, pp. 217-261, In F. D. Neidhardt (ed.), *Escherichia coli* and *Salmonella* Cellular and Molecular Biology/Second Edition, American Society for Microbiology Press, Washington, D.C; Chepuri et al., 1990, J. Biol. Chem., 265:11185-11192).

Specific examples of a gene coding for cyoA include the gene located at the nucleotide numbers 450834 to 449887 (complementary strand) of the *Escherichia coli* genomic sequence (GenBank Accession No. U00096) as the cyoA gene of *Escherichia coli*. Specific examples of a gene coding for cyoB include the gene located at the nucleotide numbers 449865 to 447874 (complementary strand) of the *Escherichia coli* genomic sequence (GenBank Accession No. U00096) as the cyoB gene of *Escherichia coli*. Specific examples of a gene coding for cyoC include the gene located at the nucleotide numbers 447884 to 447270 (complementary strand) of the *Escherichia coli* genomic sequence (GenBank Accession No. U00096) as the cyoC gene of *Escherichia coli*. Specific examples of a gene coding for cyoD include the gene located at the nucleotide numbers 447270 to 446941 (complementary strand) of the *Escherichia coli* genomic sequence (GenBank Accession No. U00096) as cyoD gene of *Escherichia coli*. Specific examples of a gene coding for cyoE include the gene located at the nucleotide numbers 446929 to 446039 (complementary strand) of the *Escherichia coli* genomic sequence (GenBank Accession No. U00096) as the cyoE gene of *Escherichia coli*.

The bacterium used for the presently disclosed subject matter may be a strain which has been modified so that the activity of pyruvate synthase or pyruvate:NADP+ oxidoreductase is increased (refer to WO2009/031565).

The "pyruvate synthase" can mean an enzyme reversibly catalyzing the following reaction, which generates pyruvic acid from acetyl-CoA and $CO_2$ in the presence of an electron donor such as ferredoxin or flavodoxin (EC 1.2.7.1). Pyruvate synthase may be abbreviated as PS, and may be designated pyruvate oxidoreductase, pyruvate ferredoxin oxidoreductase, pyruvate flavodoxin oxidoreductase, or pyruvate oxidoreductase. As the electron donor, ferredoxin or flavodoxin can be used.

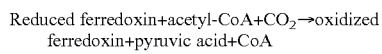

Reduced ferredoxin+acetyl-CoA+$CO_2$→oxidized ferredoxin+pyruvic acid+CoA

Enhancement of the pyruvate synthase activity can be confirmed by preparing crude enzyme solutions from the microorganism before the enhancement and the microorganism after the enhancement, and comparing the pyruvate synthase activities of them. The activity of pyruvate synthase can be measured by, for example, the method of Yoon et al. (Yoon, K. S. et al., 1997, Arch. Microbiol. 167:275-279). For example, the measurement can be attained by adding pyruvic acid to a reaction mixture containing oxidized methylviologen as an electron acceptor, CoA, and a crude enzyme solution, and spectroscopically measuring amount of reduced methylviologen, which increases due to the decarboxylation of pyruvic acid. One unit (U) of the enzymatic activity is defined as an activity of reducing 1 μmol of methylviologen per 1 minute. When the parent strain has the pyruvate synthase activity, the activity can be increased, for example, 1.5 times or more, 2 times or more, or 3 times or more, as compared to that of the parent strain. When the parent strain does not have the pyruvate synthase activity, although it is sufficient that pyruvate synthase is produced by the introduction of the pyruvate synthase gene, the activity can be enhanced to such an extent that the enzymatic activity can be measured, and the activity can be 0.001 U/mg (cell protein) or higher, 0.005 U/mg or higher, or 0.01 U/mg or higher. The pyruvate synthase is sensitive to oxygen, and activity expression and measurement thereof are generally often difficult (Buckel, W. and Golding, B. T., 2006, Ann. Rev. of Microbiol., 60:27-49). Therefore, when the enzymatic activity is measured, the enzymatic reaction with reducing oxygen concentration in a reaction vessel can be performed.

As the gene encoding pyruvate synthase, it is possible to use pyruvate synthase genes of bacteria having the reductive TCA cycle such as *Chlorobium tepidum* and *Hydrogenobacter thermophilus*. Moreover, it is also possible to use pyruvate synthase genes of bacteria belonging to the family Eenterobacteriaceae including *Escherichia coli*. Furthermore, as the gene coding for pyruvate synthase, pyruvate synthase genes of autotrophic methanogens such as *Methanococcus maripaludis*, *Methanocaldococcus jannaschii*, and *Methanothermobacter thermautotrophicus* can be used.

The "pyruvate:NADP+ oxidoreductase" means an enzyme reversibly catalyzing the following reaction, which generates pyruvic acid from acetyl CoA and $CO_2$, in the presence of an electron donor such as NADPH or NADH (EC 1.2.1.15). The pyruvate:NADP+ oxidoreductase may be abbreviated as PNO, and may be designated pyruvate dehydrogenase. However, the "pyruvate dehydrogenase activity" is the activity for catalyzing the oxidative decarboxylation of pyruvic acid to generate acetyl-CoA, as described later, and pyruvate dehydrogenase (PDH) which catalyses this reaction is an enzyme different from pyruvate:NADP+ oxidoreductase. The pyruvate:NADP+ oxidoreductase can use NADPH or NADH as the electron donor.

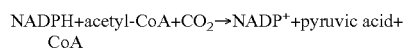

NADPH+acetyl-CoA+$CO_2$→NADP++pyruvic acid+CoA

Enhancement of the pyruvate:NADP+ oxidoreductase activity can be confirmed by preparing crude enzyme solutions from the microorganism before the enhancement and the microorganism after the enhancement, and comparing the pyruvate:NADP+ oxidoreductase activities of them. The activity of pyruvate:NADP+ oxidoreductase can be measured by, for example, the method of Inui et al. (Inui, H., et al., 1987, J. Biol. Chem., 262:9130-9135). For example, the measurement can be attained by adding pyruvic acid to a reaction mixture containing oxidized methylviologen as an electron acceptor, CoA, and a crude enzyme solution, and spectroscopically measuring the amount of reduced methylviologen, which increases due to the decarboxylation of pyruvic acid. One unit (U) of the enzymatic activity is defined as an activity of reducing 1 μmol of methylviologen per 1 minute. When the parent strain has the pyruvate:NADP+ oxidoreductase activity, the activity can increase 1.5 times or more, 2 times or more, or 3 times or more, as compared to that of the parent strain. When the parent strain does not have the pyruvate:NADP+ oxidoreductase activity, although it is sufficient that pyruvate:NADP+ oxidoreductase is produced by the introduction of the pyruvate:NADP+ oxidoreductase gene, the activity can be enhanced to such an extent that the enzymatic activity can be measured, and the activity can be 0.001 U/mg (cell protein) or higher, 0.005 U/mg or higher, or 0.01 U/mg or higher. The pyruvate:NADP+ oxidoreductase is sensitive to oxygen, and activity expression and measurement thereof are generally often difficult (Inui, H., et al, 1987, J. Biol. Chem., 262: 9130-9135; Rotte, C. et al., 2001, Mol. Biol. Evol., 18:710-720).

As for the gene coding for pyruvate:NADP+ oxidoreductase, it is known that, besides the pyruvate:NADP+ oxidoreductase gene of *Euglena gracilis*, which is a photosynthetic eukaryotic microorganism and is also classified into protozoans (Nakazawa, M. et al., 2000, FEBS Lett., 479:155-156), and the pyruvate:NADP+ oxidoreductase gene of a protist, *Cryptosporidium parvum* (Rotte, C. et al., 2001, Mol. Biol. Evol., 18:710-720), a homologous gene also exists in Bacillariophyta, *Tharassiosira pseudonana* (Ctrnacta, V. et al., 2006, J. Eukaryot. Microbiol., 53:225-231).

Specifically, the pyruvate:NADP+ oxidoreductase gene of *Euglena gracilis* can be used (GenBank Accession No. AB021127).

The microorganism of the presently disclosed subject matter may be a microorganism modified so that the pyruvate synthase activity is increased by a modification for increasing the activity of recycling the oxidized electron donor to reduced electron donor, which is required for the pyruvate synthase activity, as compared to a parent strain, for example, a wild-type or non-modified strain. Examples of the activity of recycling oxidized electron donor to reduced electron donor include the ferredoxin-NADP$^+$ reductase activity. Furthermore, the microorganism may be a microorganism modified so that the activity of pyruvate synthase is increased by such a modification that pyruvate synthase activity increases, in addition to the enhancement of the electron donor recycling activity. The aforementioned parent strain may be a strain inherently having a gene coding for the electron donor recycling activity, or a strain which does not inherently have the electron donor recycling activity, but can be imparted with the activity by introduction of a gene coding for the activity to show improved L-amino acid-producing ability.

The "ferredoxin-NADP$^+$ reductase" means an enzyme that reversibly catalyzes the following reaction (EC 1.18.1.2).

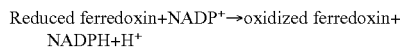

Reduced ferredoxin+NADP$^+$→oxidized ferredoxin+ NADPH+H$^+$

This reaction is a reversible reaction, and can generate the reduced ferredoxin in the presence of NADPH and the oxidized ferredoxin. Ferredoxin is replaceable with flavodoxin, and the enzyme designated flavodoxin-NADP$^+$ reductase also has an equivalent function. Existence of ferredoxin-NADP$^+$ reductase is confirmed in a wide variety of organisms ranging from microorganisms to higher organisms (refer to Carrillo, N. and Ceccarelli, E. A., 2003, Eur. J. Biochem., 270:1900-1915; Ceccarelli, E. A. et al., 2004, Biochim. Biophys. Acta., 1698:155-165), and some of the enzymes are also named ferredoxin-NADP$^+$ oxidoreductase or NADPH-ferredoxin oxidoreductase.

Enhancement of the ferredoxin-NADP$^+$ reductase activity can be confirmed by preparing crude enzyme solutions from the microorganism before the modification and the microorganism after the modification, and comparing the ferredoxin-NADP$^+$ reductase activities of them. The activity of ferredoxin-NADP$^+$ reductase can be measured by, for example, the method of Blaschkowski et al. (Blaschkowski, H. P. et al., 1982, Eur. J. Biochem., 123:563-569). For example, the activity can be measured by using ferredoxin as a substrate to spectroscopically measure the decrease of the amount of NADPH. One unit (U) of the enzymatic activity is defined as the activity for oxidizing 1 μmol of NADPH per 1 minute. When the parent strain has the ferredoxin-NADP$^+$ reductase activity, and the activity of the parent strain is sufficiently high, it is not necessary to enhance the activity. However, the enzymatic activity can be increased 1.5 times or more, 2 times or more, or 3 times or more, as compared to that of the parent strain.

Genes encoding the ferredoxin-NADP$^+$ reductase are found in many biological species, and any of them showing the activity in the objective L-amino acid-producing strain can be used. As for *Escherichia coli*, the fpr gene has been identified as a gene of flavodoxin-NADP$^+$ reductase (Bianchi, V. et al., 1993, 175:1590-1595). Moreover, it is known that, in *Pseudomonas putida*, an NADPH-putidaredoxin reductase gene and a putidaredoxin gene exist as an operon (Koga, H. et al., 1989, J. Biochem. (Tokyo), 106:831-836).

Examples of the flavodoxin-NADP$^+$ reductase gene of *Escherichia coli* include the fpr gene which is located at the nucleotide numbers 4111749 to 4112495 (complementary strand) of the genomic sequence of the *Escherichia coli* K-12 strain (Genbank Accession No. U00096). Moreover, a ferredoxin-NADP$^+$ reductase gene (Genbank Accession No. BAB99777) is also found at the nucleotide numbers 2526234 to 2527211 of the genomic sequence of *Corynebacterium glutamicum* (Genbank Accession No. BA00036).

The pyruvate synthase activity requires the presence of ferredoxin or flavodoxin as an electron donor. Therefore, the microorganism may be a microorganism modified so that the activity of pyruvate synthase is increased by such a modification that ferredoxin- or flavodoxin-producing ability is improved.

Moreover, the microorganism may also be modified so that the ferredoxin- or flavodoxin-producing ability is improved, in addition to being modified so that the pyruvate synthase activity or flavodoxin-NADP$^+$ reductase and pyruvate synthase activities are enhanced.

The term "ferredoxin" refers to a protein bound with an iron-sulfur cluster containing nonheme iron atoms (Fe) and sulfur atoms, and called 4Fe-4S, 3Fe-4S or 2Fe-2S cluster, and which functions as a one-electron carrier. "Flavodoxin" refers to a protein containing FMN (flavin-mononucleotide) as a prosthetic group and which functions as a one- or two-electron carrier. Ferredoxin and flavodoxin are described in the reference of McLean et al. (McLean K. J. et al., 2005, Biochem. Soc. Trans., 33:796-801).

The parent strains to be subjected to the modification may be strains that inherently have an endogenous gene encoding ferredoxin or flavodoxin. Alternatively, the parent strains may be strains that do not inherently have a gene encoding ferredoxin or flavodoxin, but can be imparted with the activity by introduction of a ferredoxin or flavodoxin gene to show improved L-amino acid-producing ability.

Improvement of ferredoxin- or flavodoxin-producing ability as compared to the parent strain such as a wild-type or non-modified strain can be confirmed by, for example, SDS-PAGE, two-dimensional electrophoresis or Western blotting using antibodies (Sambrook, J. et al., 1989, Molecular Cloning A Laboratory Manual/Second Edition, Cold Spring Harbor Laboratory Press, New York). Degree of the increase of the production amount is not particularly limited so long as it increases as compared to that of a wild-type strain or non-modified strain. However, it can be increased, for example, 1.5 times or more, 2 times or more, or 3 times or more, as compared to that of a wild-type or non-modified strain.

The activities of ferredoxin and flavodoxin can be measured by adding them to an appropriate oxidation-reduction reaction system. For example, a method comprising reducing produced ferredoxin with ferredoxin-NADP$^+$ reductase and quantifying reduction of cytochrome C by the produced reduced ferredoxin is disclosed by Boyer et al. (Boyer, M. E. et al., 2006, Biotechnol. Bioeng., 94:128-138). Furthermore, the activity of flavodoxin can be measured by the same method using flavodoxin-NADP$^+$ reductase.

Genes encoding ferredoxin or flavodoxin are widely distributed, and any of those can be used so long as encoded ferredoxin or flavodoxin can be utilized by pyruvate synthase and an electron donor recycling system. For example, in *Escherichia coli*, the fdx gene exists as a gene encoding ferredoxin having a 2Fe-2S cluster (Ta, D. T. and Vickery, L. E., 1992, J. Biol. Chem., 267:11120-11125), and the yfhL gene is expected as a gene encoding ferredoxin having a 4Fe-4S cluster. Furthermore, as the flavodoxin gene, the fldA gene (Osborne C. et al., 1991, J. Bacteriol., 173:1729-1737) and the fldB gene (Gaudu, P. and Weiss, B., 2000, J. Bacteriol., 182:1788-1793) are known. In the genomic sequence of *Corynebacterium glutamicum* (Genbank Accession No. BA00036), multiple ferredoxin genes, fdx (Genbank Accession No. BAB97942) were found at the nucleotide numbers of 562643 to 562963, and the fer gene was found at the nucleotide numbers of 1148953 to 1149270 (Genbank Accession No. BAB98495). Furthermore, in the *Chlorobium tepidum*, many ferredoxin genes exist, and ferredoxin I and ferredoxin II have been identified as genes for the 4Fe-4S type ferredoxin, which serves as the electron acceptor of pyruvate synthase (Yoon, K. S. et al., 2001, J. Biol. Chem., 276:44027-44036). Ferredoxin or flavodoxin genes of bacteria having the reductive TCA cycle, such as *Hydrogenobacter thermophilus*, can also be used.

Specific examples of the ferredoxin gene of *Escherichia coli* include the fdx gene located at the nucleotide numbers of 2654770 to 2655105 (complementary strand) of the genomic sequence of the *Escherichia coli* K-12 strain (Genbank Accession No. U00096), and the yfhL gene located at the nucleotide numbers of 2697685 to 2697945 of the same. Examples of the flavodoxin gene of *Escherichia coli* include the fldA gene located at the nucleotide numbers of 710688 to 710158 (complementary strand) of the genomic sequence of the *Escherichia coli* K-12 strain (Genbank Accession No. U00096), and the fldB gene located at the nucleotide numbers 3037877 to 3038398 of the same.

Examples of the ferredoxin gene of *Chlorobium tepidum* include the ferredoxin I gene located at the nucleotide numbers of 1184078 to 1184266 in the genomic sequence of *Chlorobium tepidum* (Genbank Accession No. NC_002932), and the ferredoxin II gene located at the nucleotide numbers of 1184476 to 1184664 of the same. Examples further include the ferredoxin gene of *Hydrogenobacter thermophilus* (Genbank Accession No. BAE02673) and the ferredoxin gene of *Sulfolobus solfataricus* indicated with the nucleotide numbers of 2345414 to 2345728 in the genomic sequence of *Sulfolobus solfataricus*. Furthermore, the gene may be cloned from *Chlorobium, Desulfobacter, Aquifex, Hydrogenobacter, Thermoproteus, Pyrobaculum* bacteria or the like on the basis of homology to the genes exemplified above, or those cloned from γ-proteobacteria such as those of the genera *Enterobacter, Klebsiella, Serratia, Erwinia* and *Yersinia*, coryneform bacteria such as *Corynebacterium glutamicum* and *Brevibacterium lactofermentum, Pseudomonas* bacteria such as *Pseudomonas aeruginosa, Mycobacterium* bacteria such as *Mycobacterium tuberculosis*, and so forth.

<1-2> Decreasing Activity of Enzyme in Arginine Succinyltransferase Pathway

Hereafter, the modification for decreasing activity or activities of one or two or more kinds of enzymes of the arginine succinyltransferase pathway is described.

The term "arginine succinyltransferase pathway" refers to a pathway which includes the following reaction, in which arginine is decomposed to generate glutamate and succinate in five steps (henceforth also referred to as the "AST pathway").

Arginine+succinyl coenzyme A+α-ketoglutarate+ NAD$^+$→glutamates+succinate+CoA+2NH$_3$+ CO$_2$+NADH+2H$^+$ Specifically, the reaction is catalyzed as the following five steps of the reactions.

1) AstA (arginine succinyltransferase, EC 2.3.1.109)

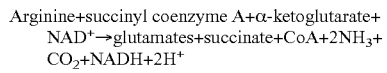

The arginine succinyltransferase can also be referred to as arginine N-succinyltransferase, arginine and ornithine N$^2$-succinyltransferase, succinyl-CoA:L-arginine 2-N-succinyltransferase, AST or AOST (J. Bacteriol., 1998, Vol. 180, No. 16, 4278-4286).

AstA is encoded by the astA gene (synonyms: ECK1745, b1747, ydjV). As the astA gene of *Escherichia coli*, there can be exemplified a gene having the nucleotide sequence shown as SEQ ID NO: 1, which is located at the nucleotide numbers 1827755 to 1828789 in the genomic sequence of *Escherichia coli* (GenBank Accession No. U00096). The amino acid sequence encoded by this gene is shown as SEQ ID NO: 2. The enzymatic activity of the arginine succinyltransferase can be measured by referring to the method of Wauven C. V. et al. (Arch. Microbiol., 1988, 150:400-404).

2) AstB (succinylarginine dihydrolase, EC 3.5.3.23)

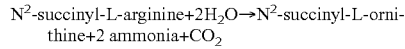

The succinylarginine dihydrolase can also be referred to as arginylsuccinate dihydrolase, N-succinylarginine dihydrolase, N$^2$-succinylarginine dihydrolase, arginine succinylhydrolase, 2-N-succinyl-L-arginine iminohydrolase, or SAD (J. Bacteriol., 1998, Vol. 180, No. 16, 4278-4286).

AstB is encoded by the astB gene (synonyms: ECK1743, b1745, ydjT). As the astB gene of *Escherichia coli*, there can be exemplified a gene having the nucleotide sequence shown as SEQ ID NO: 3, which is located at the nucleotide numbers 1824940 to 1826283 of the genomic sequence of *Escherichia coli* (GenBank Accession No. U00096). The amino acid sequence encoded by this gene is shown as SEQ ID NO: 4. The enzymatic activity of the succinylarginine dihydrolase can be measured by referring to the method of Tocilj A. et al. (J. Biol. Chem., 2005, 280:15800-15808).

3) AstC (succinylornithine aminotransferase, EC 2.6.1.81)

N$^2$-Succinyl-L-ornithine+2-oxoglutarate→N$^2$-succinyl-L-glutamate 5-semialdehyde+L-glutamate The succinylornithine aminotransferase can also be referred to as succinylornithine transaminase, N$^2$-succinylornithine 5-aminotransferase, 2-N-succinyl-L-ornithine:2-oxoglutarate 5-aminotransferase, or SOT.

AstC is encoded by the astC gene (synonyms: ECK1746, ydjW, b1748, argM, cstC, ydhW). Specifically, as the astC gene, there can be exemplified a gene having the nucleotide sequence shown as SEQ ID NO: 5, which is located at the nucleotide numbers 1828786 to 1830006 in the genomic sequence of *Escherichia coli* (GenBank Accession No. U00096). The amino acid sequence encoded by this gene is shown as SEQ ID NO: 6. The enzymatic activity of the succinylornithine aminotransferase can be measured by referring to the method of Schneider B. L. et al. (J. Bacteriol., 1998, 180:4278-4286).

4) AstD (succinylglutamate-semialdehyde dehydrogenase, EC 1.2.1.71)

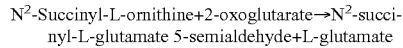

The succinylglutamate-semialdehyde dehydrogenase can also be referred to as succinylglutamic semialdehyde dehydrogenase, N-succinylglutamate 5-semialdehyde dehydrogenase or SGSDH.

AstD is encoded by the astD gene (synonyms: ECK1744, b1746, ydjU). As the astD gene of *Escherichia coli*, there can be exemplified a gene having the nucleotide sequence shown as SEQ ID NO: 7, which is locatesdat the nucleotide numbers 1826280 to 1827758 in the genomic sequence of *Escherichia coli* (GenBank Accession No. U00096). The amino acid sequence encoded by this gene is shown as SEQ ID NO: 8.

The enzymatic activity of the succinylglutamate-semialdehyde dehydrogenase can be measured by referring to the method of Schneider B. L. et al. (J. Bacteriol., 1998, 180: 4278-4286).

5) AstE (succinylglutamate desuccinylase, EC 3.5.1.96)

N$^2$-Succinylglutamate+H$_2$O→succinate+L-glutamate

The succinylglutamate desuccinylase can also be referred to as N$^2$-succinylglutamate desuccinylase or SGDS.

AstE is encoded by the astE gene (synonyms: ECK1742, b1744, ydjS). Specifically, as the astE gene of *Escherichia coli*, there can be exemplified a gene having the nucleotide sequence shown as SEQ ID NO: 9, which is located at the nucleotide numbers 1823979 to 1824947 in the genomic sequence of *Escherichia coli* (GenBank Accession No. U00096). The amino acid sequence encoded by this gene is shown as SEQ ID NO: 10. The enzymatic activity of the succinylglutamate desuccinylase can be measured by referring to the method of Itoh Y. et al., 1: J. Bacteriol., 1997 December, 179(23):7280-90.

As for *Escherichia coli*, for example, examples of the enzymes of the AST pathway include proteins having the amino acid sequence of SEQ ID NO: 2, 4, 6, 8 or 10. However, they may be those having any of these amino acid sequences, but including a conservative mutation, so long as the functions of the proteins are not changed. That is, they may be proteins having the amino acid sequences of SEQ ID NO: 2, 4, 6, 8 or 10, including substitutions, deletions, insertions, additions or the like of one or several amino acid residues.

Although the number of the "one or several" amino acid residues may differ depending on the positions in the three-dimensional structure of the protein or the types of amino acid residues, specifically, it may be, for example, 1 to 20, 1 to 10, or 1 to 5. The conservative mutation is typically a conservative substitution. The conservative substitution is a mutation wherein substitution takes place mutually among Phe, Trp, and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitutions, deletions, insertions, additions, inversions or the like may be a result of a naturally-occurring mutation or variation due to an individual difference or difference of species of a microorganism from which the genes are derived (mutant or variant). Such genes can be obtained by, for example, modifying a known nucleotide sequence of a gene by site-specific mutagenesis so that the amino acid residues at the specific sites of the encoded protein include substitutions, deletions, insertions, or additions of amino acid residues.

Furthermore, the genes coding for the enzymes of the AST pathway may be a DNA which can hybridize with a complementary sequence of the nucleotide sequence of SEQ ID NO: 1, 3, 5, 7 or 9, or a probe which can be prepared from the nucleotide sequence under stringent conditions, so long as it codes for arginine succinyltransferase, succinylarginine dihydrolase, succinylornithine aminotransferase, succinylglutamate semialdehyde dehydrogenase or succinylglutamate desuccinylase. The "stringent conditions" are conditions under which a so-called specific hybrid is formed, and a non-specific hybrid is not formed. Examples of the stringent conditions include those under which highly homologous DNAs hybridize to each other, for example, DNAs not less than 90% homologous, not less than 95% homologous, not less than 97% homologous, or not less than 99% homologous, hybridize to each other, and DNAs less homologous than the above do not hybridize to each other, and conditions of washing once, or 2 or 3 times, at a salt concentration and temperature corresponding to washing in typical Southern hybridization, i.e., 1×SSC, 0.1% SDS at 60° C., 0.1×SSC, 0.1% SDS at 60° C., or 0.1×SSC, 0.1% SDS at 68° C.

As the probe, a part of a complementary sequence of the genes can also be used. Such a probe can be prepared by PCR using oligonucleotides prepared on the basis of a known gene sequence as primers and a DNA fragment containing the nucleotide sequences as a template. Although the length of the probe is suitably chosen depending on the hybridization conditions, it is usually 100 bp to 1 kbp. For example, when a DNA fragment having a length of about 300 bp is used as the probe, the washing conditions of hybridization may be 50° C., 2×SSC and 0.1% SDS.

The phrase "modified so that activity of an enzyme of the AST pathway is decreased" can mean that the activity of the enzyme of the AST pathway per cell of the bacterium has become lower than that of a non-modified strain, such as a wild-type strain, of the bacterium belonging to the family Enterobacteriaceae. This means, for example, that number of molecules of the enzyme per cell is decreased as compared to that of the parent or wild-type strain, or that the activity of the enzyme per molecule is decreased as compared to that of the parent or wild-type strain. The enzymatic activity per cell can be compared by comparing the enzymatic activity in cell extracts of a wild-type strain or parent strain and a modified strain cultured under the same condition. The term "decrease" of the activity can include a complete disappearance of the activity. The enzyme of which activity is decreased may be any of AstA, AstB, AstC, AstD, and AstE, and may include one or two or more of these enzymes. Activity of an enzyme on the upstream side of the AST pathway can be decreased. The bacterium can be modified so that at least the activity of AstA is decreased.

The phrase "activity of an enzyme of the AST pathway is decreased" can mean that activity of the enzyme of the AST pathway in each cell of a modified strain of the bacterium is decreased to 50% or less, 30% or less, or 10% or less, of the activity of a non-modified strain, such as a wild-type strain. Examples of the wild-type strain of *Escherichia* bacterium serving as an object of the comparison include, for example, the *Escherichia coli* MG1655 strain, and so forth. Decrease of the enzymatic activities can be measured by the methods described above.

The modification for decreasing activity of an enzyme of the AST pathway can be achieved by, specifically, partially or fully deleting the astA, astB, astC, astD or astE gene on a chromosome, or modifying an expression control sequence such as a promoter or the Shine-Dalgarno (SD) sequence of the gene or an operon including the gene. The decrease of expression can include decrease of transcription and decrease of translation. Furthermore, expression of the genes can also be decreased by modifying a non-translation region other than the expression control sequence. The entire gene as well as the sequences on both sides of the gene on the chromosome can be deleted. Furthermore, modification can also be attained by introducing a mutation for amino acid substitution (missense mutation), a stop codon (nonsense mutation), or a frame shift mutation which adds or deletes one or two nucleotides into the coding region of the target gene on the chromosome (Journal of Biological Chemistry, 1997, 272:8611-8617; Proceedings of the National Academy of Sciences, USA, 1998, 95 5511-5515; Journal of Biological Chemistry, 1991, 266, 20833-20839).

It is estimated that, in *Escherichia coli*, the genes coding for the enzymes of the AST pathway constitute the astCADBE operon structure containing the structural genes astC, astA, astD, astB and astE in this order, and transcription starts from a promoter located upstream of astC (Schneider, B. L. et al., J. Bacteriol., 1998, 180, 4278-4286). Accordingly, if a nonsense mutation or a frame shift mutation is introduced into an upstream gene, downstream genes may not be normally expressed, and therefore, in order to decrease activities of two or more kinds of enzymes of the AST pathway, a nonsense mutation, frame shift mutation or deletion mutation can be introduced into an upstream region of the operon, for example, the expression control region of the ast operon, or the coding region of the astC or astA gene. For example, it is estimated that, if a mutation is introduced into the astA gene, the activities of AstD, AstB, and AstE are also decreased, in addition to the activity of AstA. In order to decrease the activities of all the enzymes of the AST pathway, for example, a mutation can be introduced into the expression control region of the ast operon or the coding region of the astCA genes.

Modification of each gene can be attained by gene recombination. Specific examples of the methods based on gene recombination include partially or fully deleting an expression control sequence such as a promoter region, a coding region, or a non-coding region of a target gene on a chromosome by utilizing homologous recombination, and introducing another sequence, a frame shift mutation, a nonsense mutation, or a missense mutation into these regions.

Modification of an expression control sequence can be performed for one or more nucleotides, two or more nucleotides, or three or more nucleotides. When a coding region is deleted, the region to be deleted may be an N-terminus region, an internal region or a C-terminus region, or even the entire coding region, so long as the function of the target protein produced from the gene is decreased or deleted. Deletion of a longer region can usually more surely inactivate a target gene. Furthermore, reading frames upstream and downstream of the region to be deleted can be different.

When another sequence is inserted into a coding region of a target gene, the sequence may be inserted into any region of the gene, and insertion of a longer sequence can usually more surely inactivate the target gene. Reading frames upstream and downstream of the insertion site can be different. The other sequence is not particularly limited so long as the chosen inserted sequence decreases or deletes the function of the encoded protein, and examples include a transposon carrying an antibiotic resistance gene, a gene useful for L-amino acid production or the like.

A target gene on the chromosome can be modified as described above by, for example, preparing a deletion-type gene of the gene, in which a partial sequence of the gene is deleted so that the deletion-type gene does not produce a protein that can normally function. Then, a bacterium can be transformed with a DNA containing the deletion-type gene to cause homologous recombination between the deletion-type gene and the native gene on the chromosome, which results in substitution of the deletion-type gene for the gene on the chromosome. The protein encoded by the deletion-type gene has a conformation different from that of the wild-type enzyme protein, if it is even produced, and thus the function is decreased or deleted. Such gene disruption based on gene substitution utilizing homologous recombination has already been established, and examples include Red-driven integration (Datsenko, K. A., and Wanner, B. L., Proc. Natl. Acad. Sci. USA, 2000, 97:6640-6645), methods using a linear DNA such as the method of utilizing Red driven integration in combination with an excision system derived from λ phage (Cho, E. H., Gumport, R. I., Gardner, J. F., J. Bacteriol., 2002, 184:5200-5203) (refer to WO2005/010175), methods using a plasmid containing a temperature sensitive replication origin or a plasmid capable of conjugative transfer, methods utilizing a suicide vector without a replication origin in a host (U.S. Pat. No. 6,303,383, Japanese Patent Laid-open No. 05-007491), and so forth.

Decrease of activity of an enzyme in the AST pathway can be confirmed by any of the enzymatic activity measurement methods described above. Decrease in transcription amount of a target gene can be confirmed by comparing amount of mRNA transcribed from the target gene with that observed in a wild-type or non-modified strain. Examples of the method for measuring amount of mRNA include Northern hybridization, RT-PCR, and so forth (Molecular Cloning, Cold spring Harbor Laboratory Press, Cold Spring Harbor (USA), 2001). Although the transcription amount may be decreased to any extent so long as it is decreased as compared to that observed in a wild-type strain or non-modified strain, it can be decreased to at least 75% or less, 50% or less, 25% or less, or 10% or less, of that observed in, for example, a wild-type strain or non-modified strain, and the gene can be not expressed at all.

Decrease in amount of a protein encoded by the target gene can be confirmed by Western blotting using antibodies that bind to the protein (Molecular Cloning, Cold Spring Harbor Laboratory Press, Cold Spring Harbor (USA) 2001). Although the amount of the protein may be decreased to any extent so long as it is decreased as compared to that observed in a wild-type strain or non-modified strain, it can be decreased to at least 75% or less, 50% or less, 25% or less, or 10% or less, of that observed in, for example, a wild-type strain or non-modified strain, and the protein can be not produced at all (the activity has completely disappeared).

A gene coding for AstA, AstB, AstC, AstD or AstE showing low activity can also be obtained by subjecting the astA, astB, astC, astD or astE gene to a mutation treatment.

Examples of the method for decreasing activity of an enzyme in the AST pathway include, besides the aforementioned genetic manipulation techniques, for example, a method of treating an *Escherichia* bacterium with ultraviolet irradiation or a mutagen used for usual mutagenesis treatment such as N-methyl-N'-nitro-N-nitrosoguanidine (NTG) or nitrous acid, and selecting a strain showing decreased activity of an enzyme in the AST pathway.

<2> Method for Producing L-Amino Acid

In the method for producing an L-amino acid of the presently disclosed subject matter, a bacterium which belongs to the family Enterobacteriaceae, and has an L-amino acid producing ability, and which has been modified so that activity or activities of one or two or more kinds of enzymes of the arginine succinyltransferase pathway is/are decreased is cultured to produce and accumulate an L-amino acid in the culture, and the L-amino acid is collected from the culture. The L-amino acid can be an amino acid of the aspartic acid family or an aromatic amino acid.

As the medium to be used, media conventionally used for the production of L-amino acids by fermentation using microorganisms can be used. That is, usual media containing a carbon source, a nitrogen source, inorganic ions, and optionally other organic components as required can be used. As the carbon source, saccharides such as glucose, sucrose, lactose, galactose, fructose, and hydrolysates of starches; alcohols such as glycerol and sorbitol; and organic acids such as fumaric acid, citric acid and succinic acid can be used. Glucose, fructose, or sucrose can be used as the carbon source in an example. In addition, a strain not having sucrose-assimilating ability can be made into a strain that can utilize sucrose as a carbon source by introducing a gene for sucrose assimilation (U.S. Pat. No. 5,175,107).

Glycerol or a fatty acid can be used as the carbon source in another example. Glycerol may be used at any concentration so long as a concentration suitable for the production of L-amino acid is chosen. When glycerol is used as a sole carbon source in the medium, it can be present in the medium in an amount of about 0.1 to 50 w/v %, about 0.5 to 40 w/v %, or about 1 to 30% w/v %. Glycerol can also be used in combination with other carbon sources such as glucose, fructose, sucrose, blackstrap molasses and starch hydrolysate. In this case, although glycerol and other carbon sources may be mixed at an arbitrary ratio, the ratio of glycerol in the carbon source can be 10% by weight or more, 50% by weight or more, or 70% by weight or more. Saccharides such as glucose, fructose, sucrose, lactose, galactose, blackstrap molasses, starch hydrolysate and a sugar solution obtained by hydrolysis of biomass, alcohols such as ethanol, and organic acids such as fumaric acid, citric acid and succinic acid can be used as the other carbon sources. Glucose is a particular example.

Although initial concentration of glycerol at the time of starting the culture can be as described above, glycerol may be supplemented with consumption of glycerol during the culture.

The glycerol can also be pure glycerol or crude glycerol. Crude glycerol is industrially produced glycerol containing impurities. Crude glycerol is industrially produced by contacting fats and oils with water under a high temperature and high pressure to hydrolyze them, or by the esterification reaction for biodiesel fuel production. Biodiesel fuel refers to fatty acid methyl esters produced from fats and oils and methanol by a transesterification reaction, and crude glycerol is produced as a by-product of this reaction (refer to Fukuda, H., Kondo, A., and Noda, H., J. Biosci. Bioeng., 2001, 92, 405-416). In the biodiesel fuel production process, the alkaline catalyst method is used for the transesterification in many cases, and acids are added for neutralization. Therefore, crude glycerol of a purity of about 70 to 95% by weight, containing water and impurities, is produced. Crude glycerol produced in the biodiesel fuel production process contains, in addition to water, impurities such as residual methanol, and salts of alkali such as NaOH as a catalyst and an acid used for neutralizing the alkali, such as $K_2SO_4$. Although it depends on manufacturers and production methods, the amount of these salts and methanol can reach several percent. The crude glycerol can contain ions derived from the alkali or the acid used for neutralization thereof, such as sodium ions, potassium ions, chloride ions, and sulfate ions, in an amount of 2 to 7%, 3 to 6%, or 4 to 5.8%, based on the weight of the crude glycerol. Although methanol may not be present as an impurity, it may be present in an amount of 0.01% or less.

The crude glycerol may further contain trace amounts of metals, organic acids, phosphorus, fatty acids, and so forth. Examples of the organic acids include formic acid, acetic acid, and so forth, and although they may not be present as impurities, they can be present in an amount of 0.01% or less. As the trace metals contained in the crude glycerol, trace metals required for growth of the microorganism can be present, and examples include, for example, magnesium, iron, calcium, manganese, copper, zinc, and so forth. Magnesium, iron, and calcium can be present in an amount of 0.00001 to 0.1%, 0.0005 to 0.1%, 0.004 to 0.05%, or 0.007 to 0.01%, in terms of the total amount based on the weight of the crude glycerol. Manganese, copper, and zinc can be present in an amount of 0.000005 to 0.01%, 0.000007 to 0.005%, or 0.00001 to 0.001%, in terms of the total amount.

The purity of the crude glycerol may be 10% or higher, 50% or higher, 70% or higher, or 80% or higher. So long as the impurities are within the aforementioned range, the purity of the glycerol may be 90% or higher.

When crude glycerol is used, the crude glycerol may be added to the medium according to the purity of the glycerol so that the amount of glycerol is within the concentration range described above. Both glycerol and crude glycerol may be added to the medium.

Fatty acid refers to a monovalent carboxylic acid of long chain hydrocarbon represented by the general formula CnHmCOOH (n+1 and m+1 represent the number of carbon atoms and the number of hydrogen atoms contained in the fatty acid, respectively). In general, a fatty acid having 12 or more carbon atoms is referred to as a long chain fatty acid in many cases. There are a variety of fatty acids with varying number of carbons and varying degree of unsaturation. It is also known that the fatty acids are constituents of oils and fats, and different types of oils and fats have different compositions of fatty acids. Myristic acid ($C_{13}H_{27}COOH$) is a saturated fatty acid having 14 carbon atoms and present in coconut oil and palm oil. Palmitic acid ($C_{15}H_{31}COOH$) is a saturated fatty acid having 16 carbon atoms and abundantly present in vegetable oils and fats in general. Stearic acid ($C_{17}H_{35}COOH$) is a saturated fatty acid having 18 carbon atoms and abundantly present in animal fats and vegetable oils. Oleic acid ($C_{17}H_{33}COOH$) is a monovalent unsaturated fatty acid having 18 carbon atoms and abundantly present in animal fats or vegetable oils. Linoleic acid ($C_{17}H_{31}COOH$) is a multivalent unsaturated fatty acid having 18 carbon atoms and two double bonds of cis-configuration at the 9th and 12th positions. As the fatty acid, a mixture of the aforementioned long chain fatty acids can also be used. When a mixture of fatty acids is used as a carbon source, the fatty acids may be mixed any mixing ratio, so long as the fatty acids are mixed at concentrations at which the bacterium used in the method of the presently disclosed subject matter can utilize them as the carbon source. A mixture of fatty acids obtained by removing glycerol from a hydrolysate of oils and fats can also be used.

In the method of the presently disclosed subject matter, a hydrolysate of fats and oils can also be used.

Fats and oils can include esters of a fatty acid and glycerol, and they can also be called triglycerides. As the fats and oils, any kinds of fats and oils including fatty oils, which refer to those in a liquid state at ordinary temperature, and fats, which refer to those in a solid state at ordinary temperature, may be used, so long as hydrolysable fats and oils are chosen. Furthermore, any of vegetable fats and oils and animal fats and oils (including fish fats or oils) can be used, and they can be used independently or as a combination of two or more kinds of them. Fats and oils used as a raw material may be pure fats and oils, or a mixture containing fats and oils and substances other than fats and oils. In the case of vegetable fats and oils, examples include, for example, a plant extract containing fats and oils and a fractionation product thereof.

Examples of animal fats and oils include, but are not limited to, butter, lard, beef tallow, mutton tallow, whale oil, sardine oil, herring oil, and so forth. Examples of vegetable fats or oils include, but not limited to, palm oil, olive oil, rapeseed oil, soybean oil, rice bran oil, walnut oil, sesame oil, peanut oil, and so forth. Palm oil is oil that can be obtained from fruits of oil palm, and has come to be widely used as biodiesel fuel in recent years, and the production amount thereof is increasing. Oil palm is a generic name for the plants classified into the genus *Elaeis* of the family Palmae. Crude palm oil generally refers to unrefined palm oil produced at oil mills, and such palm oil is traded as crude palm oil. Microalgae that accumulate oils and fats are also known (Chisti, Y, Biotechnol. Adv., 2007, 25: 294-306), fats and oils can also be extracted from alga bodies. Alga bodies also contains organic substances other than fats and oils such as saccharides, proteins or amino acids, and a mixture containing these may be hydrolyzed and used as the carbon source.

Fats and oils can be those of which fatty acid species formed by hydrolysis can be assimilated by the bacterium at a higher content. Examples of long chain fatty acid species that can be assimilated by bacteria having an L-amino acid-producing ability include lauric acid, myristic acid, palmitic acid, stearic acid, oleic acid, and so forth.

A hydrolysate of fats and oils can refer to a substance obtained by chemically or enzymatically hydrolyzing the aforementioned fats and oils, and consisting of a mixture of fatty acids and glycerol. As an industrial hydrolysis method, a continuous high temperature hydrolysis method in which fats and oils are brought into contact with water at a high temperature (250 to 260° C.) under a high pressure (5 to 6 MPa) is commonly performed. A reaction performed at low temperature (about 30° C.) by using an enzyme is also industrially used (Jaeger, K. E. et al., FEMS Microbial. Rev., 1994, 15:29-63). As the aforementioned enzyme, a lipase that catalyzes a hydrolysis reaction of fats and oils can be used. Lipases are industrially important enzymes and used for various industrial applications (Hasan, F. et al., Enzyme and Microbiol. Technol., 2006, 39:235-251). A hydrolysate of fats and oils consists of a mixture of fatty acids and glycerol, and it is known that weight ratio of glycerol to the fatty acids contained in a common hydrolysate of fats and oils such as palm oil is about 10%. The hydrolysate of fats and oils is not particularly limited so long as a hydrolysate containing fatty acids is used. For example, a hydrolysate of fats and oils can be used as it is, a hydrolysate of fats and oils a part of which fatty acids and glycerol is removed can also be used, or a hydrolysate of fats and oils to which fatty acids or glycerol is added may also be used. In such a case, the weight ratio of glycerol and fatty acids can be 5 to 20:100, or 7.5 to 15:100.

A fatty acid or hydrolysate of fats and oils may be present in the chosen medium in the method of the presently disclosed subject matter in any amount so long as the bacterium can assimilate it. However, when a fatty acid or hydrolysate of fats and oils is added to the medium as a sole carbon source, it can be present at a concentration of 10 w/v % or lower, 5 w/v % or lower, or 2 w/v % or lower, and it can be present at a concentration of 0.2 w/v % or higher, 0.5 w/v % or higher, or 1.0 w/v % or higher.

When a fatty acid or hydrolysate of fats and oils is used in a feed medium as a sole carbon source, it can be present at such a concentration that it is present in the medium after feeding at a concentration of 5 w/v % or lower, 2 w/v % or lower, or 1 w/v % or lower, and at a concentration of 0.01 w/v % or higher, 0.02 w/v % or higher, or 0.05 w/v % or higher. Concentration of a fatty acid can be measured by gas chromatography (Hashimoto, K. et al., Biosci. Biotechnol. Biochem., 1996, 70:22-30) or HPLC (Lin, J. T. et al., J. Chromatogr. A., 1998, 808:43-49).

The fatty acid or fatty acid present in a hydrolysate of fats and oils to be added to the medium can be used as an alkali metal salt of sodium, potassium, or the like, which can be micellized in water. However, solubility of a sodium salt or potassium salt of fatty acid may not be sufficient for use as a fermentation raw material. Therefore, in order that a fatty acid can be more efficiently assimilated by the bacterium having an L-amino acid-producing ability, emulsification can include a step of promoting homogenization. For example, as the emulsification method, addition of an emulsification enhancer or a surfactant can be contemplated. Examples of the emulsification enhancer referred to here can include phospholipids and sterols. Examples of the surfactant can include, as nonionic surfactants, poly(oxyethylene) sorbitan fatty acid esters such as poly(oxyethylene) sorbitan monooleic acid ester (Tween 80), alkyl glucosides such as n-octyl β-D-glucoside, sucrose fatty acid esters such as sucrose stearate, polyglycerin fatty acid esters such as polyglycerin stearic acid ester, and so forth. Examples of the surfactant can include, as ampholytic surfactants, N,N-dimethyl-N-dodecylglycine betaine, which is an alkylbetaine, and so forth. Besides these, surfactants generally used in the field of biology such as Triton X-100, polyoxyethylene(20) cetyl ether (Brij-58) and nonylphenol ethoxylate (Tergitol NP-40) can be used.

Furthermore, an operation for promoting emulsification or homogenization of fatty acid is also effective. This operation may be any operation so long as an operation that promotes emulsification or homogenization of fatty acid is chosen. Specific examples thereof include homogenizer treatments, homomixer treatments, ultrasonication, high pressure treatments, high temperature treatments, and so forth. Homogenizer treatments, ultrasonication, and combinations of them are particular examples.

A treatment with the surfactant and homogenizer treatment and/or ultrasonication in combination can be used. These treatments can be carried out under an alkaline condition where fatty acids are more stable. As the alkaline condition, pH can be not lower than 9, or not lower than 10.

As for the other ingredients to be added to the medium, in addition to the carbon source, a nitrogen source and inorganic ions, as well as other organic ingredients as required can be added. As the nitrogen source in the medium, ammonia, ammonium salts such as ammonium sulfate, ammonium carbonate, ammonium chloride, ammonium phosphate, ammonium acetate and urea, nitrates and so forth can be used. Ammonia gas or aqueous ammonia used for adjustment of pH can also be used as the nitrogen source. Peptone, yeast extract, meat extract, malt extract, corn steep liquor, soybean hydrolysate and so forth can also be used. The medium may contain one of these nitrogen sources, or two or more of them. These nitrogen sources can be used in both starting medium and feed medium. Furthermore, the same nitrogen source may be used in both the starting medium and feed medium, or nitrogen source of the feed medium may be different from nitrogen source of the starting medium.

The medium can contain a phosphoric acid source and a sulfur source in addition to the carbon source and the nitrogen source. As the phosphoric acid source, potassium dihydrogenphosphate, dipotassium hydrogenphosphate, phosphoric acid polymers such as pyrophosphoric acid and so forth can be utilized. Although the sulfur source may be any substance containing sulfur atoms, sulfuric acid salts such as sulfates, thiosulfates and sulfites, and sulfur-containing amino acids such as cysteine, cystine and glutathione can be used, and ammonium sulfate can be used in another example.

Furthermore, the medium may contain a growth-promoting factor (nutrient having a growth promoting effect) in addition to the carbon source, nitrogen source and sulfur source. As the growth promoting factor, trace metals, amino acids, vitamins, nucleic acids as well as peptone, casamino acid, yeast extract, soybean protein degradation product and so forth containing the foregoing substances can be used. Examples of the trace metals include iron, manganese, magnesium, calcium and so forth. Examples of the vitamins include vitamin $B_1$, vitamin $B_2$, vitamin $B_6$, nicotinic acid, nicotinamide, vitamin $B_{12}$ and so forth. These growth-promoting factors may be contained in the starting medium or the feed medium.

Furthermore, when an auxotrophic mutant strain that requires an amino acid or the like for growth thereof is used, a required nutrient can be supplemented to the medium. In particular, since the L-lysine biosynthetic pathway is enhanced and L-lysine-degrading ability is often attenuated in L-lysine-producing bacteria as described above, one or more types of substances selected from L-threonine, L-homoserine, L-isoleucine and L-methionine can be added. The starting medium and the feed medium may have the same composition or different compositions. Furthermore, when the feed medium is fed at multiple stages, the compositions of the feed media fed at the stages may be the same or different.

The culture can be performed as aeration culture at a fermentation temperature of 20 to 45° C., or 33 to 42° C. The culture can be performed with controlling the oxygen concentration to be about 5 to 50%, or about 10%. Furthermore, pH can be controlled to be 5 to 9. If pH of the medium is lowered during the culture, calcium carbonate can be added, or the medium can be neutralized with an alkaline such as ammonia gas and aqueous ammonia. If culture is performed under such conditions as described above, for example, for about 10 to 120 hours, a marked amount of L-amino acid can be accumulated in the culture medium. Although the concentration of L-amino acid accumulated is not limited so long as it is higher than that observed with a wild-type strain, and it enables isolation and collection of the L-amino acid from the medium, it can be 50 g/L or higher, 75 g/L or higher, or 100 g/L or higher.

In order to maintain the accumulation of L-amino acid at a certain level or higher, the culture of the bacterium may be carried out as separate seed culture and main culture. The seed culture may be carried out with shaking using a flask or the like or as batch culture, and the main culture may be carried out as fed-batch culture or continuous culture. Both the seed culture and main culture may be carried out as batch culture.

When the objective amino acid is a basic amino acid, the production may be performed by a method in which fermentation is performed by controlling pH of the medium during culture to be 6.5 to 9.0 and pH of the medium at the end of the culture to be 7.2 to 9.0 and controlling the pressure in the fermentation tank to be positive during the culture, or by supplying carbon dioxide gas or a mixed gas containing carbon dioxide gas to the medium to provide a culture period where the medium contains 20 mM or more of bicarbonate ions and/or carbonate ions, so that these bicarbonate ions and/or carbonate ions serve as counter ions of cations mainly consisting of a basic amino acid, and the objective basic amino acid is then collected (Japanese Patent Laid-open No. 2002-065287).

The L-amino acid can be collected from fermentation broth by a combination of conventionally known methods such as ion-exchange resin method (Nagai, H. et al., Separation Science and Technology, 39(16), 3691-3710), precipitation, membrane separation (Japanese Patent Laid-open Nos. 9-164323 and 9-173792), crystallization (WO2008/078448, WO2008/078646), and other methods. When the L-amino acid accumulates in the cells, the cells can be disrupted with, for example, ultrasonic waves or the like, and the L-amino acid can be collected by the ion exchange resin method or the like from the supernatant obtained by removing the cells from the cell-disrupted suspension by centrifugation.

The L-amino acid collected may contain bacterial cells, medium components, moisture, and by-product metabolites of the bacterium in addition to the objective L-amino acid. Purity of the collected L-amino acid may be 50% or higher, 85% or higher, or 95% or higher (Japanese Patent No. 1214636, U.S. Pat. Nos. 5,431,933, 4,956,471, 4,777,051, 4,946,654, 5,840,358, 6,238,714, U.S. Patent Published Application No. 2005/0025878).

Furthermore, when L-amino acid precipitates into the medium, it can be collected by centrifugation, filtration or the like. L-Amino acid precipitated in the medium and L-amino acid dissolved in the medium may be isolated together after the L-amino acid dissolved in the medium is crystallized.

Furthermore, L-phenylalanine produced by the method of the presently disclosed subject matter can be used for, for example, producing a lower alkyl ester of α-L-aspartyl-L-phenylalanine (also referred to as "aspartame"). Therefore, the present invention also provides a method for producing a lower alkyl ester of α-L-aspartyl-L-phenylalanine using L-phenylalanine as a starting material. This method comprises the step of synthesizing a lower alkyl ester of α-L-aspartyl-L-phenylalanine from L-phenylalanine produced by the aforementioned method, and aspartic acid or a derivative thereof. Examples of the lower alkyl ester include methyl ester, ethyl ester, propyl ester, and so forth.

The method for synthesizing a lower alkyl ester of α-L-aspartyl-L-phenylalanine from L-phenylalanine and aspartic acid or its derivative is not particularly limited, so long as L-phenylalanine or its derivative is used for the synthesis of the lower alkyl ester of α-L-aspartyl-L-phenylalanine. Specifically, for example, a lower alkyl ester of α-L-aspartyl-L-phenylalanine can be produced by the following method (U.S. Pat. No. 3,786,039). L-Phenylalanine is esterified to obtain a lower alkyl ester of L-phenylalanine. The L-phenylalanine alkyl ester is reacted with an L-aspartic acid derivative of which 3-carboxyl group is protected and α-carboxyl group is esterified and thereby activated. Examples of such a derivative include N-acyl-L-aspartic anhydride such as N-formyl-, N-carbobenzoxy-, or N-p-methoxycarbobenzoxy-L-aspartic anhydride. By this condensation reaction, a mixture of N-acyl-α-L-aspartyl-L-phenylalanine and N-acyl-3-L-aspartyl-L-phenylalanine is obtained. If the condensation reaction is performed in the presence of an organic acid of which acid dissociation constant at 37° C. is $10^{-4}$ or less, the ratio of the α-isomer to the 3-isomer in the mixture is increased (Japanese Patent Laid-Open No. 51-113841). Then, the N-acyl-α-L-aspartyl-L-phenylalanine is separated from the mixture, and hydrogenated to obtain α-L-aspartyl-L-phenylalanine.

EXAMPLES

Hereinafter, the present invention will be still more specifically explained with reference to examples.

Example 1

Construction of L-Lysine-Producing Bacterium Showing Decreased Activity of Enzyme in Ast Pathway <1-1> Construction of Strain in which astA Gene Coding for Arginine Succinyltransferase is Disrupted First, by using an *Escherichia coli* wild-type strain, MG1655 strain, an arginine succinyltransferase non-producing strain was constructed. PCR was performed by using pMW118(attL-Cm-attR) plasmid (described in U.S. Pat. No. 7,306,933) as a template and the synthetic oligonucleotides shown in SEQ ID NOS: 11 and 12 having a sequence corresponding to the both ends of the attachment sites of λ phage, attL and attR, at the 3' ends of the oligonucleotides and a sequence corresponding to a part of the astA gene as the target gene at the 5' ends of the oligonucleotides as primers. By using the amplified product, MG1655ΔastA::att-Cm strain was constructed according to the λ-red method described in U.S. Pat. No. 7,306,933. In the λ-red method, a Cm resistant recombinant strain was obtained by culturing the strain obtained above at 37° C. as plate culture on the L-agar medium containing Cm (chloramphenicol, 40 mg/L), and selecting a strain that formed a colony. The obtained astA gene-disrupted strain was designated MG1655ΔastA::att-Cm strain. In the MG1655ΔastA::att-Cm strain, a part of the coding region of the astA gene on the genome is replaced with the Cm resistance gene.

<1-2> Construction of Ast-Deficient L-Lysine-Producing Bacterium

From the MG1655ΔastA::att-Cm strain obtained in <1-1>, P1 lysate was obtained in a conventional manner. By using this P1 lysate and an L-lysine-producing bacterium *E. coli* WC196ΔcadAΔldcC strain (FERM BP-11027) constructed by the method described in U.S. Patent Published Application No. 2006/0160191 as a host, WC196ΔcadAΔldcCΔastA::att-Cm strain was constructed by the P1 transduction method using the chloramphenicol resistance as a marker. Then, this strain was transformed with the plasmid pCABD2 for L-lysine production carrying the dapA, dapB and lysC genes (International Patent Publication WO01/53459) in a conventional manner to construct WC196ΔcadAΔldcCΔastA::att-Cm/pCABD2 strain as a chloramphenicol-resistant and streptomycin-resistant recombinant strain. The chloramphenicol-resistant and streptomycin-resistant recombinant strain was obtained by culturing the strain constructed above at 37° C. as plate culture on the L-agar medium containing Cm (chloramphenicol, 40 mg/L) and Sm (streptomycin, 20 mg/L), and selecting a strain that formed a colony. As a comparative strain, the WC196ΔcadAΔldcC strain was used.

These strains were each cultured at 37° C. in the L medium containing 20 mg/L of streptomycin until final $OD_{600}$ of about 0.6 was obtained, then an equal volume of 40% glycerol solution was added to the medium, and the mixture was stirred. Then, the mixture was divided into appropriate volumes, stored at −80° C., and used as glycerol stocks.

Example 2

Evaluation of L-Lysine-Producing Ability of AST Pathway-Blocked L-Lysine-Producing Bacterium The glycerol stocks of the strains obtained in Example 1 were thawed, 100 μL of each stock was uniformly applied to an L plate containing 20 mg/L of streptomycin, and culture was performed at 37° C. for 24 hours as stationary culture. The cells corresponding to about ¼ of the cells obtained on the plate were suspended in 0.5 mL of physiological saline, and turbidity was measured at a wavelength of 600 nm by using a spectrophotometer U-2000 (Hitachi, Ltd.). The suspension containing the obtained bacterium was inoculated in 40 mL of the fermentation medium (described below) containing 20 mg/L of streptomycin contained in a 500-mL volume Erlenmeyer flask with baffle in such a volume that the final $OD_{600}$ became 0.2, and culture was performed at 37° C.
for 48 hours at a revolution number of 200 rpm for stirring on a rotary shaking culture machine, InnOva 4430 (New Brunswick Scientific).

As the carbon source for the main culture, sodium oleate, glucose or glycerol was used, and as the emulsification enhancer, poly(oxyethylene)sorbitan monooleic acid ester (Tween 80, Nakarai-Tesque) was added at a final concentration of 0.5% (w/v). The total carbon source amount was 10 g/L. It was separately confirmed that *Escherichia coli* could not assimilate Tween 80 by using the M9 minimal medium (refer to Current Protocols in Molecular Biology, Ausubel, F. A. et al., John Wiley & Sons Inc., New York).

The culture was performed for 48 hours under the aforementioned conditions, and the amount of L-lysine accumulated in the medium was measured by using Biotech Analyzer AS310 (Sakura Seiki). Consumption of the total carbon source added to the medium was separately confirmed by using a gas chromatograph GC-2014 (Shimadzu) in the case of the oleic acid ester, Biotech Analyzer AS310 in the case of glucose, or Biotech Analyzer BF-5 (Oji Scientific Instruments) in the case of glycerol. Furthermore, Tween 80 was added at a final concentration of 1.0% (w/v) immediately after the end of the culture, then the medium was diluted, and turbidity was measured at a wavelength of 600 nm by using a spectrophotometer U-2000 (Hitachi, Ltd.) to measure cell amount at the time of the end of the culture.

The composition of the fermentation medium used for the main culture is shown below (unit: g/L or % (in terms of volume/volume), all values are final concentrations). As the carbon source, sodium oleate (first grade, Junsei Chemical), glucose or reagent glycerol was used.

| | |
|---|---|
| (1) Carbon source | 10 g/L |
| (adjusted to pH 7.5 with HCl and autoclaved at 120° C. for 20 minutes) | |
| (2) Tween 80 | 0.5% |
| (sterilized using Nalgene 0.45 μm filter (Nalge)) | |
| (3) $MgSO_4 \cdot 7H_2O$ | 1 g/L |
| (autoclaved at 120° C. for 20 minutes) | |
| (4) $(NH_4)_2SO_4$ | 16 g/L |
| $KH_2PO_4$ | 1 g/L |
| $FeSO_4 \cdot 7H_2O$ | 0.01 g/L |
| $MnSO_4 \cdot 4H_2O$ | 0.082 g/L |
| Yeast extract (Difco) | 2 g/L |
| ($(NH_4)_2SO_4$, $KH_2PO_4$, $FeSO_4 \cdot 7H_2O$, $MnSO_4 \cdot 4H_2O$ and yeast extract were mixed, adjusted to pH 7.5 with KOH, and autoclaved at 120° C. for 20 minutes) | |
| (5) PIPES (pH 7.5) | 20 g/L |
| (adjusted to pH 7.5 with NaOH and autoclaved at 120° C. for 20 minutes) | |

Solutions of the ingredients of the aforementioned five groups (1) to (5) separately sterilized were mixed to prepare the fermentation medium containing sodium oleate, glucose or glycerol as the carbon source.

The results of the main culture are shown in Table 1 (in the column of L-lysine (g/L), amounts of L-lysine accumulated in the medium are indicated). After the end of the culture, all the carbon sources were consumed in the media. As seen from the results shown in Table 1, the astA-deficient strain, WC196ΔcadAΔldcCΔastA::att-Cm/pCABD2, showed significantly improved L-lysine accumulation rates with all the carbon sources, as compared to the WC196ΔcadAΔldcC/pCABD2 strain, which was not deficient in the astA gene.

TABLE 1

| Carbon source | Strain | L-lysine (g/L) | OD$_{600}$ |
|---|---|---|---|
| Oleate | WC196ΔcadAΔldcC/pCABD2 | 4.52 | 8.16 |
| Oleate | WC196ΔcadAΔldcCΔastA::att-Cm/pCABD2 | 4.88 | 7.13 |
| Glucose | WC196Δ cadAΔldcC/pCABD2 | 4.09 | 5.21 |
| Glucose | WC196ΔcadAΔldcCΔastA::att-Cm/pCABD2 | 4.25 | 5.50 |
| Glycerol | WC196Δ cadAΔldcC/pCABD2 | 4.22 | 4.37 |
| Glycerol | WC196ΔcadAΔldcCΔastA::att-Cm/pCABD2 | 4.50 | 4.44 |

Explanation of Sequence Listing
SEQ ID NO: 1: Nucleotide sequence of astA gene
SEQ ID NO: 2: Amino acid sequence of AstA
SEQ ID NO: 3: Nucleotide sequence of astB gene
SEQ ID NO: 4: Amino acid sequence of AstB
SEQ ID NO: 5: Nucleotide sequence of astC gene
SEQ ID NO: 6: Amino acid sequence of AstC
SEQ ID NO: 7: Nucleotide sequence of astD gene
SEQ ID NO: 8: Amino acid sequence of AstD
SEQ ID NO: 9: Nucleotide sequence of astE gene
SEQ ID NO: 10: Amino acid sequence of AstE
SEQ ID NO: 11: Primer for astA disruption
SEQ ID NO: 12: Primer for astA disruption

INDUSTRIAL APPLICABILITY

According to the present invention, L-amino acids can be efficiently produced.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid, which comprises culturing an *Escherichia coli* bacterium having an L-amino acid-producing ability in a medium to produce and accumulate an L-amino acid in the medium, and collecting the L-amino acid from the medium, wherein the bacterium has been modified so that an activity or activities of one or more enzyme(s) of the arginine succinyltransferase pathway is/are decreased, wherein the enzyme of the arginine succinyltransferase pathway is selected from the group consisting of arginine succinyltransferase, succinylarginine dihydrolase, succinylornithine aminotransferase, succinylglutamate-semialdehyde dehydrogenase, succinylglutamate desuccinylase, and combinations thereof, wherein the arginine succinyltransferase is selected from the group consisting of: (A) a protein having the amino acid sequence of SEQ ID No:2, (B) a protein having the amino acid sequence of SEQ ID No:2, but includes substitutions, deletions, insertions, or additions of 1-10 amino acid residues, and (C) combinations thereof;

wherein the succinylarginine dihydrolase is selected from the group consisting of: (A) a protein having the amino acid sequence of SEQ ID No:4, (B) a protein having the amino acid sequence of SEQ ID No:4, but includes substitutions, deletions, insertions, or additions of 1-10 amino acid residues, and (C) combinations thereof;

wherein the succinylornithine aminotransferase is selected from the group consisting of: (A) a protein having the amino acid sequence of SEQ ID No:6, (B) a protein having the amino acid sequence of SEQ ID No:6, but includes substitutions, deletions, insertions, or additions of 1-10 amino acid residues, and (C) combinations thereof;

wherein the succinylglutamate-semialdehyde dehydrogenase is selected from the group consisting of: (A) a protein having the amino acid sequence of SEQ ID No:8, (B) a protein having the amino acid sequence of SEQ ID No:8, but includes substitutions, deletions, insertions, or additions of 1-10 amino acid residues, and (C) combinations thereof;

wherein the succinylglutamate desuccinylase is selected from the group consisting of: (A) a protein having the amino acid sequence of SEQ ID No:10, (B) a protein having the amino acid sequence of SEQ ID No:10, but includes substitutions, deletions, insertions, or additions of 1-10 amino acid residues, and (C) combinations thereof; and wherein the L-amino acid is selected from the group consisting of L-lysine, L-threonine, and combinations thereof; and wherein the activity or activities of the one or more enzyme(s) of the arginine succinyltransferase pathway is/are decreased by a method selected from the group consisting of decreasing expression of a gene or genes encoding for the one or more enzymes, disrupting a gene or genes encoding for the one or more enzymes, and combinations thereof.

2. The method according to claim 1, wherein the arginine succinyltransferase, succinylarginine dihydrolase, succinylornithine aminotransferase, succinylglutamate-semialdehyde dehydrogenase, and succinylglutamate desuccinylase are proteins encoded by astA, astB, astC, astD, and astE genes, respectively.

3. The method according to claim 1, wherein the bacterium has been modified so that at least the arginine succinyltransferase activity is decreased by decreasing expression of the gene that encodes arginine succinyltransferase, or by disrupting the gene that encodes arginine succinyltransferase.

4. The method according to claim 1, wherein the L-amino acid is L-lysine.

5. The method according to claim 1, wherein the medium comprises a fatty acid or glycerol as a carbon source.

* * * * *